United States Patent
Agus et al.

(10) Patent No.: US 6,262,111 B1
(45) Date of Patent: Jul. 17, 2001

(54) METHOD FOR INCREASING THE CONCENTRATION OF ASCORBIC ACID IN BRAIN TISSUES OF A SUBJECT

(75) Inventors: David B. Agus, Brooklyn; Juan C. Vera; David W. Golde, both of New York, all of NY (US)

(73) Assignee: Sloan-Kettering Institute for Cancer Research, New york, NY (US)

(*) Notice: Subject to any disclaimer, the term of this patent is extended or adjusted under 35 U.S.C. 154(b) by 0 days.

(21) Appl. No.: 09/449,516

(22) Filed: Nov. 24, 1999

Related U.S. Application Data

(63) Continuation-in-part of application No. 09/443,785, filed on Nov. 19, 1999, which is a continuation of application No. PCT/US98/10608, filed on May 21, 1998.
(60) Provisional application No. 60/067,185, filed on Dec. 1, 1997, and provisional application No. 60/047,271, filed on May 21, 1997.

(51) Int. Cl.⁷ .................................................. A61K 31/34
(52) U.S. Cl. ............................................................ 514/474
(58) Field of Search ................................................ 514/474

(56) References Cited

U.S. PATENT DOCUMENTS

| | | |
|---|---|---|
| 4,229,430 | 10/1980 | Fahim et al. |
| 4,414,202 | 11/1983 | Silvetti |
| 4,620,979 | 11/1986 | Schachar |
| 4,705,804 | 11/1987 | Geho et al. |
| 4,722,937 | 2/1988 | Jacob et al. |
| 4,772,470 | 9/1988 | Inoue et al. |
| 4,778,679 | 10/1988 | Silvetti |
| 4,822,816 * | 4/1989 | Markham .............................. 514/474 |
| 4,929,378 | 5/1990 | Morita et al. |
| 4,968,716 | 11/1990 | Markham |
| 5,021,452 | 6/1991 | Labbe et al. |
| 5,070,085 | 12/1991 | Markham |
| 5,114,972 | 5/1992 | Ohnishi |
| 5,122,536 | 6/1992 | Perricone |
| 5,151,419 | 9/1992 | Perenyi et al. |
| 5,166,233 | 11/1992 | Kuroya et al. |
| 5,192,550 | 3/1993 | Edgren et al. |
| 5,192,808 | 3/1993 | Ruehl et al. |
| 5,270,336 | 12/1993 | Marciniak et al. |
| 5,281,196 | 1/1994 | Sultenfuss |
| 5,380,761 | 1/1995 | Szabo et al. |
| 5,444,095 | 8/1995 | Tatton et al. |
| 5,470,874 | 11/1995 | Lerner |
| 5,547,995 | 8/1996 | Filhol et al. |
| 5,612,208 * | 3/1997 | Nakanishi et al. ..................... 435/189 |
| 5,770,215 * | 6/1998 | Moshyedi .............................. 424/440 |
| 5,827,886 | 10/1998 | Hersh |
| 5,935,596 | 8/1999 | Crotty et al. |
| 6,133,317 * | 6/1998 | Hart ....................................... 514/574 |

FOREIGN PATENT DOCUMENTS

| | | |
|---|---|---|
| 0129343 | 12/1984 | (EP) |
| 0347864 | 12/1989 | (EP) |
| 0493985 | 6/1999 | (EP) |
| WO98/52560 | 11/1998 | (WO) |

OTHER PUBLICATIONS

Wilson, Can J. Physiol. Pharmacol., vol. 75, No. 11–12, pp. 1149–1163 (abstract), Nov. 1997.*

Agus et al. J. Clin. Invest., vol. 100, No. 11, pp. 2842–2848, Dec. 1997.*

Welch et al, The American Society of Biochemistry and Molecular Biology, vol. 270, No. 21, pp. 12584–12592, 1995.*

Vera et al, The American Society of Biolchemistry and Molecular Biology, vol. 270, No. 40, pp. 23705–23712, 1995.*

Ngkeekwong et al, J. Biochem., vol. 324, pp. 225–230, 1997.*

Siushansian et al, J. Neurochem., vol. 68. pp. 2378–2385 (abstract), 1997.*

Challem, Jack, "Vitamin E: High–Doses Reduce The Risk Of Heart Attack" *The Nutrition Reporter* (May 1996) pp. 1–3.

Department of Neurology, University of Rochester Medical Center, "Effects Of Tocopherol And Deprenyl On The Progression Of Disability In Early Parkinson's Disease. The Parkinson Study Group" *The New England Journal Of Medicine* (Jan. 21, 1993) vol. 328(3):176–183.

Diaz, Marco, N., et al., "Antioxidants And Atherosclerotic Heart Disease" *The New England Journal of Medicine* (Aug. 7, 1997) vol. 337:408–416.

Drachman, David, A., "Treatment Of Alzheimer's Disease—Searching For A Breakthrough, Settling For Less" *The New England Journal Of Medicine* (Apr. 24, 1997) vol. 336:1245–1247.

(List continued on next page.)

*Primary Examiner*—James H. Reamer
(74) *Attorney, Agent, or Firm*—John P. White; Cooper & Dunham LLP

(57) ABSTRACT

This invention provides a method for increasing the concentration of ascorbic acid in the cells of a subject which comprises administering to the subject an amount of dehydroascorbic acid effective to increase the concentration of ascorbic acid in the subject's cells. This invention further provides a method for increasing the antioxidant potential of the cells of a subject which comprises administering to the subject an amount of dehydroascorbic acid effective to increase the antioxidant potential of the subject's cells. This invention also provides a method for increasing the concentration of ascorbic acid in brain tissue of a subject which comprises administering to the subject an amount of dehydroascorbic acid effective to increase the concentration of ascorbic acid in the subject's brain tissue. This invention also provides a method for increasing the antioxidant potential of brain tissue of a subject which comprises administering to the subject an amount of dehydroascorbic acid effective to increase the antioxidant potential of the subject's brain tissue.

12 Claims, 11 Drawing Sheets

OTHER PUBLICATIONS

Hayashi, Eiichi, et al., "Fundamental Studies on Physiological and Pharmacological Actions of L–Ascorbate 2–Sulfate (IV) On the General Pharmacological Acitons of L–Ascorbate 2–Sulfate" *Oyo Yakuri* 129(1): 131–138, 1976.

Jenner, P., "Oxidative Damage In Neurodegenerative Disease" *The Lancet* (Sep. 17, 1994) vol. 344:796–798n.

Lethem, Rosemary, et al., "Antioxidants and Dementia" *The Lancet* (Apr. 26, 1997) vol. 349:1189–1190.

Patterson, John, W., "The Diabetogenic Effect of Dehydroascorbic and Dehydroisoascorbic Acids", *J. Biol. Chem.* 183: 81–88, 1950.

Patterson, John, ., et al. "Some Effects of Dehydroascorbic Acid on the Central Nervous System", *Am. J. Physiol.* 167: 119–126, 1951.

Peyser, C.E., et al., "Trial Of D–Alpha– Tocopherol In Huntington's Disease" *American Journal of Psychiatry* (Dec. 1995) vol. 152(12):1771–1775.

Sano, Mary, et al., "A Controlled Trial Of Selegiline, Alpha–Tocopherol, Or Both As Treatment For Alzheimer's Disease" *The New England Journal Of Medicine* (Apr. 24, 1997) vol. 336: 1216–1222.

Siostrand, "Pharmacological Effects of Dehydroascorbic Acid and Ascorbic Acid in Conscious and Anaesthetized Animals" *Acta Physiol. Scand. Suppl.* 356:1–79, 1970.

Smith, M. A., et al., "Oxidative Damage In Alzheimer's " *Nature* (Jul. 11, 1996) vol. 382:120–121.

Sorg, Olivier, et al., "Inhibition Of Astrocyte Glutamate Uptake By Reactive Oxygen Species: Role Of Antioxidant Enzymes" *Molecular Medicine* (Jul. 7, 1997) vol. 3:431–440.

Tardif, Jean–Claude, et al., "Probucol And Multivitamins In The Prevention Of Restenosis After Coronary Angioplasty" *The New England Journal Of Medicine* (Aug. 7, 1997) vol. 337:365–372.

Vera, Juan Carlos, et al., "Mammalian Facilitative Hexose Transporters Mediate The Transport Of Dehydroascorbic Acid" *Nature* (Jul. 1, 1993) vol. 364:79–82.

Witztum, Joseph, L., "The Oxidation Hypothesis Of Atherosclerosis" *The Lancet* (Sep. 17, 1994) vol. 344:793–795.

Youdim, Moussa, B.H., et al., "Understanding Parkinson's Disease" *Scientific American* (Jan. 1997) pp. 52–59.

* cited by examiner-

though it inhibits oxidative deamination, delays the onset of the disability (31). 5) Peyser et al. concluded that antioxidant therapy may slow the rate of motor decline early in the course of Huntington's disease (35). 6) According to Challem (32) free radicals and oxidative stress may be factors involved with the pathogenesis of Mad Cow disease. 7) The oxidative modification of low-density lipoprotein (LDL), termed lipid peroxidation has been shown to be an initiating event in atherosclerosis. Probucol, an antioxidant, is effective in reducing the rate of restenosis after balloon coronary angioplasty (36). Oxidized LDL has several detrimental effects on cells including brain cells such as cytotoxicity and vascular dysfunction.

METHOD FOR INCREASING THE CONCENTRATION OF ASCORBIC ACID IN BRAIN TISSUES OF A SUBJECT

This application is a continuation-in-part of U.S. Ser. No. 09/443,785, filed Nov. 19, 1999, which is a continuation of PCT International Application No. PCT/US98/10608, filed May 21, 1998, claiming priority of of U.S. Provisional Application Nos. 60/067,185, filed Dec. 1, 1997 and 60/047,271, filed May 21, 1997, the contents of which are hereby incorporated by reference into this application.

Throughout this application, various references are referred to by arabic numerals within parentheses. Disclosures of these publications in their entireties are hereby incorporated by reference into this application to more fully describe the state of the art to which this invention pertains. Full bibliographic citation for these references may be found at the end the specification, immediately preceding the claims.

This invention was made with support under Grant Nos. RO1 CA30388 and RO1 HL42107 from the National Institutes of Health. Accordingly, the United States Government has certain rights in the invention.

BACKGROUND OF THE INVENTION

Numerous connections have been made between the generation and presence of oxidative free radicals in brain tissue and neurological disorders. For example, 1) Jenner (26) links oxidative stress to Parkinson's, Alzheimer's and Huntington's diseases. 2) Recent clinical studies have demonstrated that alpha-tocopherol (vitamin E) and selegiline (deprenyl), pharmacologic agents that have antioxidant activity, can slow the progression of moderately severe Alzheimer's disease (27). 3) Antioxidants such as vitamin C and vitamin E may have an important role in the treatment of diseases whose pathogenesis involves free radical formation and impaired antioxidant defenses in the aging population. Oxidative damage has been hypothesized as central to the neurodegenerative processes such as Alzheimer's disease (28). According to the free radical hypothesis, Alzheimer's disease is an acceleration of the normal aging process in affected brain regions which become progressively more damaged by free radicals generated from metabolism. In Alzheimer's disease, the cerebral cortex seems to have increased antioxidant requirements, increased sensitivity to free radicals, and levels of the free radical defense enzymes, such as superoxide dismutase, that are reduced by 25–35% in the frontal cortex and hippocampus. The loss of hippocampal cholinergic neurons is a key feature of Alzheimer's disease and these neurons seem particularly vulnerable to the deleterious effects of free radicals on the muscarinic cholinergic receptor (29). 4) Antioxidants have been tested as drugs for Parkinson's disease (30), and it was found that selegiline, which may act as an antioxidant since Therefore, increasing the concentration of free-radical scavengers or antioxidants in brain tissue may provide therapeutic benefits to subjects suffering from neurodegenerative diseases. Sano et al. conclude (27) that the use of the antioxidants, selegiline or vitamin E may delay clinically important functional deterioration in patients with Alzheimer's disease. Their results are particularly significant because vitamin E does not cross the blood-brain barrier in large amounts, and still it has a measurable effect.

The enhancement of the antioxidant potential is useful in treating of many diseases. For example, the increase of antioxidant potential achieved by this invention will be able to treat stroke and neurovascular diseases. It is known that ischemic stroke is the most common neurologic disorder causing death or disability among adults. Strokes of all types rank third as a cause of death, surpassed only by heart disease and cancer. Ischemic stroke events account for approximately 85% of all strokes. Because no medical or surgical treatment has yet been established as reversing the effects of acute ischemic stroke, early identification and treatment of persons at the time they present with stroke is compelling, if such a treatment is efficacious. Currently, there are no approved treatments for stroke. The damage from stroke is caused by occlusion of a vessel, thereby restricting the delivery of oxygen in the blood to an area of the brain. Much of the damage is caused by damage from oxygen free radicals in the area served by the occluded vessel after reperfusion of the affected area (37). Thus, increasing the antioxidant potential of the brain may have beneficial effects on stroke and other neurovascular diseases.

Therefore, increasing vitamin C concentrations in the brain by providing dehydroascorbic acid to the subject could enhance antioxidant potential in the central nervous system and may be therapeutic in stroke and neurovascular diseases as described.

Researchers have proposed that atherosclerosis, and its deadly effects of heart attack and stroke, develops in relationship to oxidation of low-density lipoproteins (LDL) carrying cholesterol in the blood. The theory states that free radicals generated by the body's own immune cells oxidize LDL which is taken up by cells of the vascular intima initiating the atherosclerosis lesion. Ultraviolet and gamma radiation, cigarette smoke and other environmental pollutants, also cause oxidative damage to cells and vital compounds. The damage leads to the development of several chronic diseases including cancer and coronary heart disease (CHD). It was further proposed that antioxidants such as vitamin E and C and the carotenoids could prevent damage and the ensuing diseases. Many epidemiologic and animal studies have offered evidence to support the theory (33, 34). Recent studies demonstrated that the antioxidant proburol is effective in reducing the rate of restenosis after balloon coronary angioplasty (36).

Evidence suggests that the neuropathology of Huntington's disease, a neuropsychiatric disorder, results from excessive activation of glutamate-gated ion channels, which kills neurons by oxidative stress. It was reported that antioxidant therapy may slow the rate of motor decline early in the course of Huntington's disease (35).

Vitamin C enters cells, in vitro, through the facilitative glucose transporter GLUT1 in the form of dehydroascorbic acid and is retained intracellularly as ascorbic acid (1). In order to test the hypothesis that GLUT1 transport of dehydroascorbic acid is a primary physiological mechanism for tissue acquisition of vitamin C, we investigated the transport of vitamin C across the blood-brain barrier (BBB) in rodents. GLUT1 is expressed at the BBB on endothelial cells and is responsible for glucose entry into the brain. Ascorbic acid, the predominant form of vitamin C in blood, was incapable of crossing the BBB while dehydroascorbic acid readily entered the brain and was retained in the form of ascorbic acid. The transport of dehydroascorbic acid into the brain was competitively inhibited by D-glucose, but not by L-glucose. These findings define the transport of dehydroascorbic acid by GLUT1 as the mechanism by which the brain acquires vitamin C, and point to the oxidation of vitamin C as the important regulatory step in the accumulation of the vitamin by the brain.

Dehydroascorbic acid, the oxidized form of vitamin C, was previously found to be transported through the facilitative glucose transporters. Expression of GLUT1, GLUT2, and GLUT4 in *Xenopus oocytes* conferred the ability to take up dehydroascorbic acid which was retained intracellularly after it was reduced to ascorbic acid (1). It was also established that facilitative glucose transporters are involved in the transport and accumulation of vitamin C by normal human neutrophils and the myeloid leukemia cell line, HL60 (1–3). In these cells dehydroascorbic acid is transported across the cell membrane and accumulated in the reduced form, ascorbic acid, which is not transportable through the bidirectional glucose transporter (1–3). Ascorbic acid may be transported through a $Na^+$-ascorbate co-transporter that is reported to be present in small intestine, kidney and adrenomedullary chromaffin cells (4). The co-transporter has not been molecularly characterized and no $Na^+$-dependent ascorbic acid uptake in white blood cells has been found (2,3).

GLUT1 is expressed on endothelial cells at the BBB and is responsible for glucose transport into the brain (5,6). In the 1880's, Ehrlich found that intravenously injected aniline dyes colored all of the organs of experimental rabbits except the brain and the spinal cord (7,8). This observation led to the eventual discovery that the BBB is comprised of a wall of capillaries forming an endothelial barrier between the blood and the brain, functioning primarily to regulate the transport of nutrients and waste products (9,10). Several nutrient transporters have been identified at the BBB including GLUT1, a monocarboxylic acid transporter, neutral amino acid transporter, amine transporter, basic amino acid transporter, nucleoside transporter, and purine base transporter (11). Here it is shown in rodents that vitamin C crosses the BBB through GLUT1 only in the oxidized form, dehydroascorbic acid, and is retained in the brain in the reduced form, ascorbic acid.

The present invention allows for the controlled introduction of the antioxidant vitamin C into brain tissue, which should serve as an important therapeutic method to treat and prevent various disorders associated with free radicals and oxidative damage.

SUMMARY OF THE INVENTION

This invention provides a method for increasing the concentration of ascorbic acid in a cell which comprises contacting the cell with an amount of dehydroascorbic acid effective to increase the concentration of ascorbic acid in the cell. This invention also provides a method for increasing the antioxidant potential in a cell which comprises contacting the cell with an amount of dehydroascorbic acid effective to increase the antioxidant potential in the cell.

In one embodiment, the cell is a brain cell. In one embodiment, the cell is present in a tissue. In one embodiment, the tissue is a brain tissue. This invention provides the above method wherein the cell is present in a subject and the contacting is effected by administering the dehydroascorbic acid to the subject.

This invention also provides a method for increasing the concentration of ascorbic acid in the cells of a subject which comprises administering to the subject an amount of dehydroascorbic acid effective to increase the concentration of ascorbic acid in the subject's cells. This invention further provides a method for increasing the antioxidant potential of the cells of a subject which comprises administering to the subject an amount of dehydroascorbic acid effective to increase the antioxidant potential of the subject's cells.

This invention provides a method for increasing the concentration of ascorbic acid in brain tissue of a subject which comprises administering to the subject an amount of dehydroascorbic acid effective to increase the concentration of ascorbic acid in the subject's brain tissue.

This invention also provides a method for increasing the antioxidant potential of brain tissue of a subject which comprises administering to the subject an amount of dehydroascorbic acid effective to increase the antioxidant potential of the subject's brain tissue. This invention provides a method for treating or preventing dementia in a subject comprising administering to the subject an amount of dehydroascorbic acid effective to increase the concentration of ascorbic acid in the subject's brain tissue so as to thereby treat or prevent dementia in the subject.

This invention provides a method for treating or preventing dementia in a subject comprising administering to the subject an amount of dehydroascorbic acid effective to increase the antioxidant potential of the subject's brain tissue so as to thereby treat or prevent dementia in the subject.

This invention also provides a method for treating or preventing diseases involving free radicals in a subject comprising administering to the subject an amount of dehydroascorbic acid effective to increase the concentration of ascorbic acid in the subject's cells so as to thereby treat or prevent diseases involving free radicals in the subject.

This invention also provides a method for treating or preventing diseases involving free radicals in a subject comprising administering to the subject an amount of dehydroascorbic acid effective to increase the antioxidant potential of cells so as to thereby treat or prevent diseases involving free radicals in the subject.

This invention also provides a method of prophylaxis for these diseases. The diseases include but are not limited to cancer, a cardiovascular disease and cataracts.

This invention also provides a method for slowing the aging process of a subject comprising administering to the subject an amount of dehydroascorbic acid effective to increase the antioxidant potential of cells so as to thereby slow the aging process in the subject.

This invention also provides a method for treating a subject infected with human immunodeficiency virus comprising administering to the subject an amount of dehydroascorbic acid effective to treat the subject infected with human immunodeficiency virus.

This invention provides a method for treating or preventing a neurodegenerative disease in a subject comprising administering to the subject an amount of dehydroascorbic acid effective to increase the concentration of ascorbic acid in the subject's brain tissue so as to thereby treat or prevent a neurodegenerative disease in the subject.

This invention also provides a method for treating or preventing a neurodegenerative disease in a subject comprising administering to the subject an amount of dehydroascorbic acid effective to increase the antioxidant potential of the subject's brain tissues so as to thereby treat or prevent a neurodegenerative disease in the subject.

This invention provides a method for treating or preventing stroke or neurovascular disease or other diseases which can be caused by lipid peroxidation in a subject comprising administering to the subject an amount of dehydroascorbic acid effective to increase the concentration of ascorbic acid in the subject's brain tissue so as to thereby treat or prevent stroke or neurovascular disease or other diseases which can be caused by lipid peroxidation in the subject.

This invention also provides a method for treating or preventing stroke or neurovascular disease or other diseases which can be caused by lipid peroxidation in a subject comprising administering to the subject an amount of dehydroascorbic acid effective to increase the antioxidant potential of the brain tissues so as to thereby treat or prevent stroke or neurovascular disease or other diseases which can be caused by lipid peroxidation in the subject.

Moreover, this invention provide a method for treating or preventing central nervous system manifestations of genetic diseases.

This invention provides a method for preventing or treating behavioral disorders in a subject comprising administering to the subject an amount of dehydroascorbic acid effective to increase the concentration of ascorbic acid in the subject's brain tissue so as to thereby prevent or treat behavioral disorders in the subject.

This invention also provides a method for preventing or treating behavioral disorders in a subject comprising administering to the subject an amount of dehydroascorbic acid effective to increase the antioxidant potential of the subject's brain tissue so as to thereby prevent or treat behavioral disorders in the subject.

This invention provides the above methods which further comprise administering to the subject a therapeutically effective amount of a second agent.

BRIEF DESCRIPTION OF THE DRAWINGS

FIG. 3 Brain digital autoradiography of rat with $^{14}$C-labeled ascorbic acid, dehydroascorbic acid, D-deoxyglucose and sucrose. (A) Digital autoradiography was performed on a Fisher F344 rat (8 wks of age) 3 min after intravenous injection with 40 $\mu$Ci of $^{14}$C-dehydroascorbic acid, (B) 40 $\mu$Ci $^{14}$C-ascorbic acid and (C) 40 $\mu$Ci $^{14}$C-sucrose ([glucose-$^{14}$C(U)]-sucrose, specific activity, 310 mCi/mmol, Dupont NEN). The area of the brain is denoted with an * in the figure. The photo-stimulated luminescence (PSL)/mm$^2$ ratio of brain/background counts for the dehydroascorbic acid-injected rat was 8.6±0.3 (mean of 3 sections±SEM). The PSL/mm$^2$ ratio in the ascorbic acid-injected rat was 1.5±0.1 and 1.4±0.1 in the sucrose-injected rat.

Figure 1A:
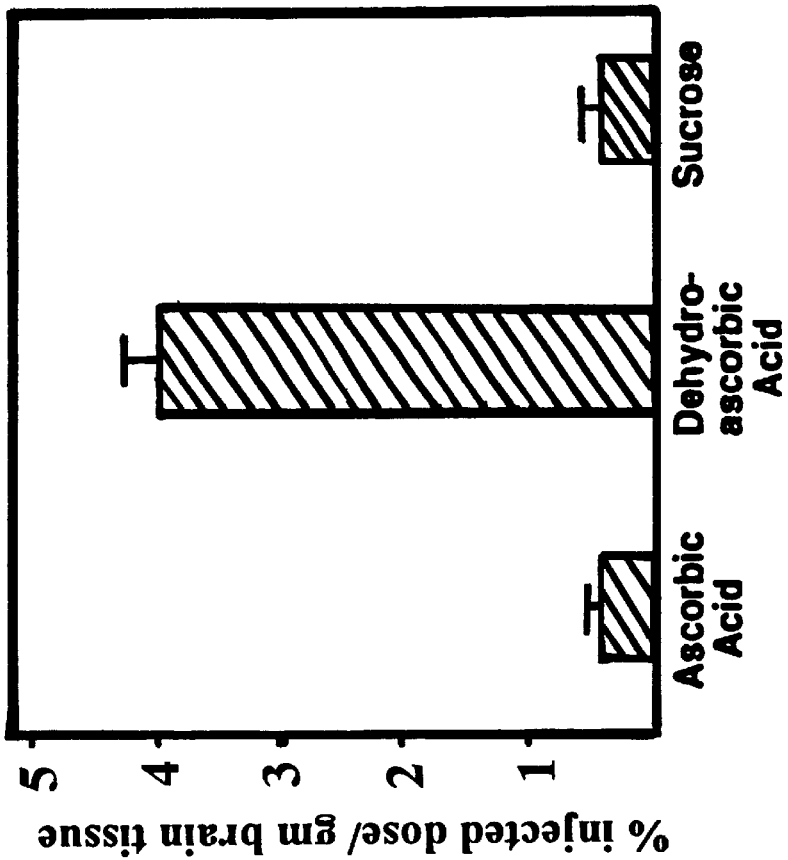
FIG. 1 Dehydroascorbic acid is transported across the BBB and accumulates in the brain as ascorbic acid. (A) Balb/c mice (age 6–8 weeks) and (B) Fischer F344 rats (70–80 gram body weight) were injected into the tail vein with 5 $\mu$Ci(mouse) or 10 $\mu$Ci(rat) $^{14}$C-ascorbic acid (L-[1-$^{14}$C]-ascorbic acid, specific activity, 6.6 mCi/mmol, Dupont NEN), $^{14}$C-dehydroascorbic acid or $^{3}$H-sucrose ([fructose-1-$^{3}$H]-sucrose, specific activity 20.0 Ci/mmol, Dupont NEN). Each group consists of 12 animals and the values are expressed as mean±SEM. (C)HPLC analysis of the methanol soluble fraction of the brain and (H) serum of a mouse injected with 20 $\mu$Ci $^{14}$C-dehydroascorbic acid and sacrificed at 5 min (injected material, hashed line). (C) Accumulation of vitamin C in the brain is in the form of ascorbic acid (~90&; retention time≈11.80 min, solid line). (H) Radioactivity present in serum is in the form of ascorbic acid (>98%; retention time≈11.80 min, solid line). (D) The initial kinetics and (E) 2 hr kinetics of accumulation of radioactivity in the brain of mice injected intravenously with $^{14}$C-ascorbic acid (●), $^{14}$C-dehydroascorbic acid (■) or $^{3}$H-sucrose (○). (F) The initial kinetics and (G) 2 hr kinetics of radioactivity in the serum of mice injected intravenously with $^{14}$C-ascorbic acid(●), $^{14}$C-dehydroascorbic acid (■) or $^{3}$H-sucrose(○). Each data set in (D) through (G) represents 4 mice±SEM.

A Both high (250 mg/kg) and low dose (40 mg/kg) DHA pre-treatment of animals undergoing reperfused stroke, demonstrated a dose-dependent improvement in post-ischemic cerebral perfusion compared to both sucrose and ascorbic acid treated animals (19±3% vehicle, 13±1% AA, 28±2% low-DHA, 40±4% high-DHA; p<0.05 for either DHA vs. either control).

B DHA conferred dose-dependent cerebroprotection as evidenced by both decreased cerebral infarct volumes (54±6% vehicle, 58±4% AA, 22±4% low-DHA, 12±4% high-DHA; p<0.05 for either DHA vs. either control)

C Reductions in neurological deficit scores (4.0±0.2 vehicle, 2.7±0.7 AA, 1.6±0.2 low-DHA, 1.9±0.2 high-DHA; p<0.05 for either DHA vs. vehicle).

D Ascorbic acid treatment was not associated with significant improvements in either infarct size or neurological function, nor did ascorbic acid treatment reduce overall mortality as was the case with DHA.

DETAILED DESCRIPTION OF THE INVENTION

This invention provides a method for increasing the concentration of ascorbic acid in a cell which comprises contacting the cell with an amount of dehydroascorbic acid effective to increase the concentration of ascorbic acid in the cell. This invention also provides a method for increasing the antioxidant potential in a cell which comprises contacting the cell with an amount of dehydroascorbic acid effective to increase the antioxidant potential in the cell.

In one embodiment, the cell is a brain cell. In one embodiment, the cell is present in a tissue. In one embodiment, the tissue is a brain tissue. In one embodiment, the cell is present in a subject and the contacting is effected by administering the dehydroascorbic acid to the subject. In one embodiment, the subject is a human.

This invention also provides a method for increasing the concentration of ascorbic acid in the cells of a subject which comprises administering to the subject an amount of dehydroascorbic acid effective to increase the concentration of ascorbic acid in the subject's cells. This invention further provides a method for increasing the antioxidant potential of the cells of a subject which comprises administering to the subject an amount of dehydroascorbic acid effective to increase the antioxidant potential of the subject's cells.

This invention provides a method for increasing the concentration of ascorbic acid in brain tissue of a subject which comprises administering to the subject an amount of dehydroascorbic acid effective to increase the concentration of ascorbic acid in the subject's brain tissue.

This invention also provides a method for increasing the antioxidant potential of brain tissue of a subject which comprises administering to the subject an amount of dehydroascorbic acid effective to increase the antioxidant potential of the subject's brain tissue.

There are several ways that dehydroascorbic acid can enter a cell of a tissue, one of which is through a facilitative glucose transporter.

The cells of the subject invention include but are not limited to brain cells, neuronal cells, endothelial cells, glial cells, microglial cells, smooth muscle cells, somatic cells, bone marrow cells, liver cells, intestinal cells, germ cells, myocytes, mononuclear phagocytes, tumor cells, and stem cells. The cell may also be another kind of cells not explicitly listed herein. In the preferred embodiment, the cells are brain cells.

The subject may be a mammal or non-mammal. The subject may be a human, a primate, an equine, an opine, an avian, a bovine, a porcine, a canine, a feline, a murine, a mouse, a rat, or a cow. The subject may also be another kind of subject not explicitly listed here. In another embodiment, the subject is a vertebrate. In a preferred embodiment, the mammal is a human being.

In one embodiment of the subject invention, the subject is afflicted with a neurodegenerative disease. Such neurodegenerative diseases include but are not limited to Alzheimer's Disease, Parkinson's Disease or other forms of presenile dementia.

In one embodiment of the subject invention, the subject is afflicted with neurovascular disease. The neurovascular disease of the present invention includes but is not limited to stroke.

The subject may carry genetic diseases with central nervous system manifestations. In an embodiment, the genetic disease is the Huntington's disease.

In one embodiment of the present invention, the subject may be afflicted with a disease which involves the oxidative modification of low-density lipoprotein peroxidase. These diseases include but are not limited to stroke, atherosclerosis and neurodegenerative disorders.

In another embodiment, the human subject is afflicted with a behavioral disorder. Such behavioral disorders include but are not limited to dysthymia, involution depression, aggressiveness via dominance, hyperactivity, deprivation syndrome, separation anxiety, intermittent anxiety, instrumental sociopathy, stereotypies, phobia or a socialization disorder. In a further embodiment, the subject is afflicted with schizophrenia.

This invention provides a method for treating or preventing dementia in a subject comprising administering to the subject an amount of dehydroascorbic acid effective to increase the concentration of ascorbic acid in the subject's brain tissue so as to thereby treat or prevent dementia in the subject.

This invention provides a method for treating or preventing dementia in a subject comprising administering to the subject an amount of dehydroascorbic acid effective to increase the antioxidant potential of the subject's brain tissue so as to thereby treat or prevent dementia in the subject.

This invention also provides a method for treating or preventing diseases involving free radicals in a subject comprising administering to the subject an amount of dehydroascorbic acid effective to increase the concentration of ascorbic acid in the subject's cells so as to thereby treat or prevent diseases involving free radicals in the subject.

This invention also provides a method for treating or preventing diseases involving free radicals in a subject comprising administering to the subject an amount of dehydroascorbic acid effective to increase the antioxidant potential of cells so as to thereby treat or prevent diseases involving free radicals in the subject. This invention also provides a method of prophylaxis for these diseases. The diseases include but are not limited to cancer, a cardiovascular disease and cataracts.

These cancers include but are not limited to the following: prostate cancer; biliary tract cancer; brain cancer, including glioblastomas and medelloblastomes; breast cancer; cervical cancer; choriocarcinoma; colon cancer; endometrial cancer; esophageal cancer; gastric cancer; hematological neoplasms, including acute lymphocytic and myelogenous leukemia, multiple myeloma, AIDS associated leukemias and adult T-cell leukemia lymphoma; intraepithelial neoplasms, including Bowens' disease and Paget's disease; liver cancer; lung cancer; lymphomas, including Hodgkin's disease and lymphozytic lymphomas; neuroblastomas; oral cancer, including squamous cell carcinoma; ovarian cancer, including those arising from epithelial cells, stromal cells, germ cells and mesenchymal cells; pancreas cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including terminal tumors (seminoma, non-seminoma (teratomas, choriocarcinomas)), stromal tumors and germ cell tumors; thyroid cancer, including thyroid adenocarcinoma and medullar carcinoma; and renal cancer including adenocarcinoma and Wilms tumor.

The cardiovascular conditions include but are not limited to artheresclerosis, post-myocardial infarction, stroke, post-angioplasty and an association with thrombolytic reperfusion.

The cataracts conditions include but are not limited to corneal opacification.

This invention also provides a method for slowing the aging process of a subject comprising administering to the subject an amount of dehydroascorbic acid effective to increase the antioxidant potential of cells so as to thereby slow the aging process in the subject.

As used herein, "aging" means accumulation of oxidative damage over time.

This invention also provides a method for treating a subject infected with human immunodeficiency virus comprising administering to the subject an amount of dehydroascorbic acid effective to treat the subject infected with human immunodeficiency virus.

As used herein, human immunodeficiency virus can be abbreviated as "HIV" and includes but is not limited to HIV-1. HIV includes but is not limited to extracellular virus particles and the forms of HIV found in HIV-1 infected cells. The modes of treatment include but are not limited to inhibiting the growth of the virus, decreasing the ability of the virus to enter cells, and also decreasing T-cell deficiency.

As it will be easily appreciated by persons of skill in the art, this invention is applicable to both human and animal diseases which could be treated by antioxidants. This invention is intended to be used in husbandry and veterinary medicine.

In this invention, the dehydroascorbic acid may be administered orally, intravenously, subcutaneously, intramuscularly, topically, or by other routes or circumstances of administration by which the dehydroascorbic acid will not be hydrolyzed. Dehydroascorbic acid hydrolyses easily in aqueous solution. It is the intention of this invention to administer the dehydroascorbic acid in a stabilized form. It is known that dehydroascorbic acid is stable under low pH conditions. Accordingly, dehydroascorbic acid may be stored in low pH and then administered directly to a large vein of a subject. Alternatively, dehydroascorbic acid may be stored in powdered form and hydrated before administering to a subject.

Moreover, dehydroascorbic acid may be encapsulated in liposomes at low pH. The encapsulated dehydroascorbic acid will then be administered to a subject. In a preferred embodiment, the encapsulated dehydroascorbic acid is administered orally.

U.S. Pat. No. 4,822,816 describes uses of aldono-lactones and salts of L-threonic, L-xylonic and L-lyxonic to stabilize the dehydroascorbic acid. The content of U.S. Pat. No. 4,822,816 is hereby incorporated into this application by reference. Accordingly, this method provides another means for stabilization of the dehydroascorbic acid.

Finally, appropriate amounts of ascorbic acid and ascorbate oxidase may be administered together to a subject to produce an amount of dehydroascorbic acid effective to increase the concentration of ascorbic acid in the brain tissues of the subject. Ascorbate oxidase catalyzes oxidation of L-ascorbic acid, and it is commercially available. U.S Pat. No. 5,612,208 describes a new ascorbate oxidase and its gene, the content of which is hereby incorporated into this application by reference. Accordingly, ascorbate oxidase may be produced by recombinant DNA technology.

Using this invention, the brain tissues of a subject may be loaded with the maximum amount of ascorbic acid.

Dehydroascorbic acid may exist in various salt forms. It is the intention of this invention to encompass these forms. The salts upon hydration will generate dehydroascorbic acid.

This invention provides a method for treating or preventing a neurodegenerative disease in a subject comprising administering to the subject an amount of dehydroascorbic acid effective to increase the concentration of ascorbic acid in the subject's brain tissue so as to thereby treat or prevent a neurodegenerative disease in the subject.

This invention also provides a method for treating or preventing a neurodegenerative disease in a subject comprising administering to the subject an amount of dehydroascorbic acid effective to increase the antioxidant potential of the subject's brain tissues so as to thereby treat or prevent a neurodegenerative disease in the subject. The neurodegenerative diseases include but are not limited to Alzheimer's Disease and Parkinson's Disease.

This invention provides a method for treating or preventing stroke or neurovascular disease or other diseases which can be caused by lipid peroxidation in a subject comprising administering to the subject an amount of dehydroascorbic acid effective to increase the concentration of ascorbic acid in the subject's brain tissue so as to thereby treat or prevent stroke or neurovascular disease or other diseases which can be caused by lipid peroxidation in the subject.

This invention also provides a method for treating or preventing stroke or neurovascular disease or other diseases which can be caused by lipid peroxidation in a subject comprising administering to the subject an amount of dehydroascorbic acid effective to increase the antioxidant potential of the brain tissues so as to thereby treat or prevent stroke or neurovascular disease or other diseases which can be caused by lipid peroxidation in the subject.

These diseases include but are not limited to stroke, atherosclerosis and neurodegenerative disorders.

Moreover, this invention provides a method for treating or preventing central nervous system manifestations of genetic diseases. The conditions of the disease will be improved by increasing the antioxidant potential of the brain. Prevention of such central nervous system manifestations of genetic disease may even be effected if the antioxidant potential of the brain is maintained at a high level. These genetic diseases include but are not limited to Huntington's disease.

This invention provides a method for preventing or treating behavioral disorders in a subject comprising administering to the subject an amount of dehydroascorbic acid effective to increase the concentration of ascorbic acid in the subject's brain tissue so as to thereby prevent or treat behavioral disorders in the subject.

This invention also provides a method for preventing or treating behavioral disorders in a subject comprising administering to the subject an amount of dehydroascorbic acid effective to increase the antioxidant potential of the subject's brain tissue so as to thereby prevent or treat behavioral disorders in the subject. Such behavioral disorders include but are not limited to dysthymia, involution depression, aggressiveness via dominance, hyperactivity, deprivation syndrome, separation anxiety, intermittent anxiety, instrumental sociopathy, stereotypies, phobia or a socialization disorder. In another embodiment, the behavioral disorder is schizophrenia.

This invention provides the above methods which further comprise administering to the subject a therapeutically effective amount of a second agent.

When treating or preventing the behavioral disorders, dehydroascorbic acid may be used in combination with other drugs. They may be administered concomitantly or at different time points. This invention also provides the above methods further comprising administering to the subject a therapeutically effective amount of a second agent.

This invention also provides a combination therapy wherein an effective amount of dehydroascorbic acid is administered with therapeutic agents for the neurodegenerative disease. The administration may be performed concomitantly or at different time points. When treating the Alzheimer's disease, the therapeutic agents include, but are not limited to, Estrogen, Vitamin E (alpha-tocopherol), Tacrine (Tetrahydroacridinamine), Selegiline (Deprenyl), and Aracept (Donepezil). With respect to the Parkinson's disease, the therapeutic agents include, but are not limited to, the anticholinergic class of drugs, clozapine, levodopa with carbidopa or benserazide, Selegiline (Deprenyl), and dopamine agonist class of drugs.

This invention will be better understood from the Experimental Details which follow. However, one skilled in the art will readily appreciate that the specific methods and results discussed are merely illustrative of the invention as described more fully in the claims which follow thereafter.

Experimental Details

Experimental Methods

Blood-brain barrier transport studies. $^{14}$C-dehydroascorbic acid was generated in all experiments by incubating the $^{14}$C-ascorbic acid with ascorbate oxidase, 1 unit/1.0 mmol L-ascorbate (derived from Cucurbita species, Sigma). Dithiothreitol (0.1 mmol/liter) was added to the vitamin C preparations as a reducing agent. Animals were sacrificed at various time points after injection by cervical dislocation of $CO_2$ inhalation. The brain was then dissected out and homogenized in 70% methanol. Samples were processed for scintillation spectrometry or HPLC as described (2,3). HPLC was performed on the methanol fraction with 1 mmol/L EDTA added (2,3). Samples were stored at −70° C. until analysis. HPLC samples were separated on a Whatman strong anion exchange Partisil 10 SAX (4.6−×25-cm) column (Whatman, Hillsboro, Oreg.). A Whatman-type WCS solvent-conditioning column was used and the eluates monitored with a Beckman System Gold liquid chromatograph (Beckman Instruments, Irvine, Calif.) with a diode array detector and radioisotope detector arranged in series. Ascorbic acid was monitored by absorbance at 265 nm and by radioactivity. Dehydroascorbic acid shows no absorbance at 265 nm and was monitored by radioactivity.

Digital autoradiography. Animals were sacrificed, frozen in a dry ice/hexane mixture and then embedded in ~5% carboxymethylcellulose (Sigma Aldrich). The animal blocks were allowed to equilibrate for ~12 hours at −20° C. and the animals were sectioned in coronal cuts with a slice thickness of ~40–45 μm in a cryo-microtome (PMV), and tape lifted for direct exposure onto digital plates (23). The exposure time was approximately 72 hours. All digital plates were scanned on a Fuji Bas 5000 digital autoradiographic system (Fuji, Inc.) At 25 μm resolution.

Calculation of the BBB permeability-surface area product. The amount of compound which crosses the BBB is dependent on two parameters defined by the following equation:

$$PS = \frac{V_D - V_0}{t}$$

where PS is the BBB permeability-surface area product and AUC is the plasma area under the concentration time-activity curve at a given time (t) after injection. A variant of the single intravenous injection technique termed the external organ technique was used to quantify the BBB PS product in anesthetized animals. The plasma and brain radioactivity was measured as decays per min (DPM)/μl of serum (after the ascorbic acid or sucrose was solubilized from the cells in the presence of 70% methanol) which was equivalent to the integral of the plasma radioactivity. The BBB PS product is calculated:

% injected dose/gm of brain tissue=PS×AUC where the variables are defined, as follows: t=time $$V_D = \frac{\frac{[^{14}C\text{-}AA \text{ or } DHA]dpm}{gm \text{ brain tissue}} (\text{brain})}{\frac{[^{14}C\text{-}AA \text{ or } DHA]dpm}{\mu l \text{ serum}} (\text{external organ})}$$

$$V_0 = \frac{\frac{[^3H\text{-}Sucrose]dpm}{gm \text{ brain tissue}} (\text{brain})}{\frac{[^3H\text{-}Sucrose]dpm}{\mu l \text{ serum}} (\text{external organ})}$$

The rats were anesthetized with a mixture of ketamine 90 mg/kg and xylazine 10 mg/kg anesthesia during the procedure. The xylazine causes a hyperglycemia and hypoinsulinemia in the animals with the serum glucose measured at approximately 280 mg/dl 30 min after induction of anesthesia (24,25). This is almost three-fold higher than baseline glucose concentrations in the rats and affects transport through GLUT1 and therefore the PS calculations. Radiolabeled test compound ($^3$H-sucrose, $^{14}$C-ascorbic acid, $^{14}$C-dehydroascorbic acid) was injected into a cannulated femoral vein in groups of 3 rats. Sucrose was used as a $V_0$ marker (plasma volume marker). For 30 seconds (t) after injection arterial blood was collected by gravity from a catheter cannulated in the abdominal aorta and then the animal was sacrificed and the brain harvested.

Results and Discussions

Figure 1B:
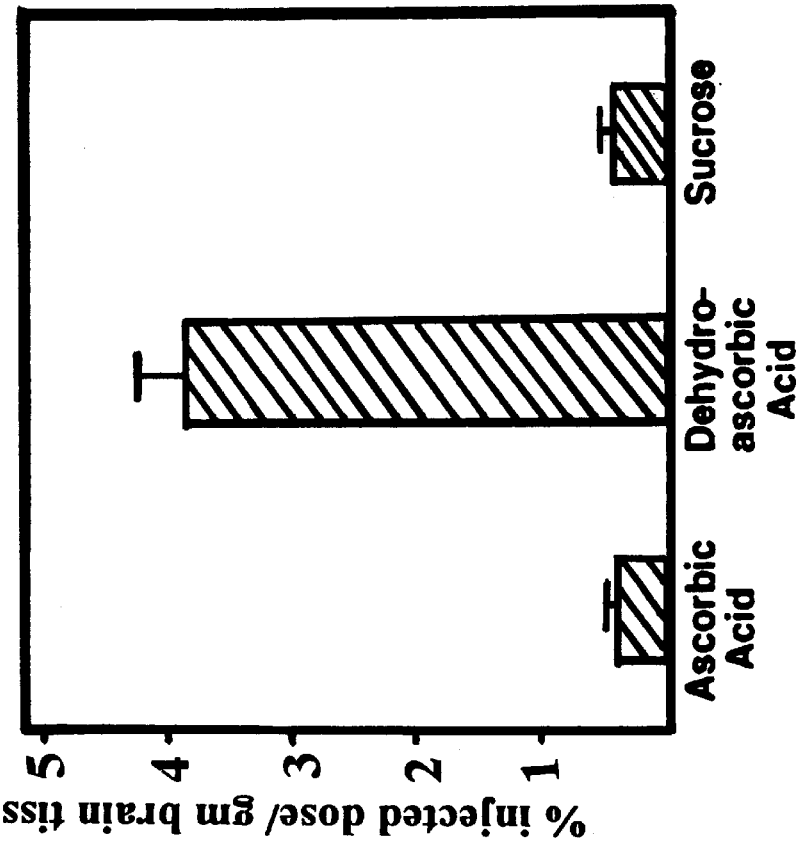

Mice and rats were injected into the tail vein with $^{14}$C-ascorbic acid, $^{14}$C-dehydroascorbic acid or $^3$H-sucrose. Three min after intravenous injection the animals were sacrificed, the brains harvested and the methanol soluble fraction counted by liquid scintillation. Approximately 4% of the dehydroascorbic acid (expressed as percent of injected dose (ID) per gram of brain tissue) was found in the brain after 3 min (FIGS. 1A and 1B). Injected ascorbic acid and sucrose yielded only trace radioactivity in the brain homogenate at 3 min, indicating that ascorbic acid could not pass the BBB. Because sucrose is not metabolized or transported it is used as a marker of plasma volume (12). The small amount of radioactivity present in the brain of the sucrose and ascorbic acid-injected animals was consistent with the radioactivity being present within the brain blood vessels. High-performance liquid chromatography (HPLC) analysis of the methanol (70%) fraction of the brain homogenate showed that the form of the vitamin C accumulated in the brain of dehydroascorbic acid-injected animal was >85% ascorbic acid (FIG. 1C). This result indicated that dehydroascorbic acid was transported across the BBB and retained as ascorbic acid in the brain.

Figure 1D:
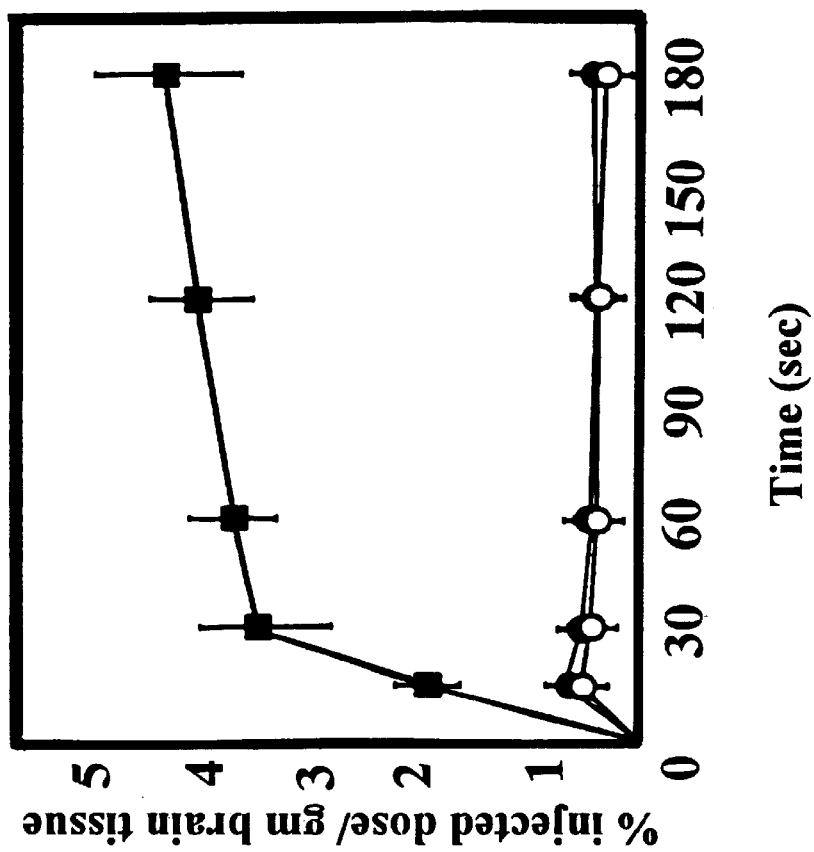
Figure 1C:
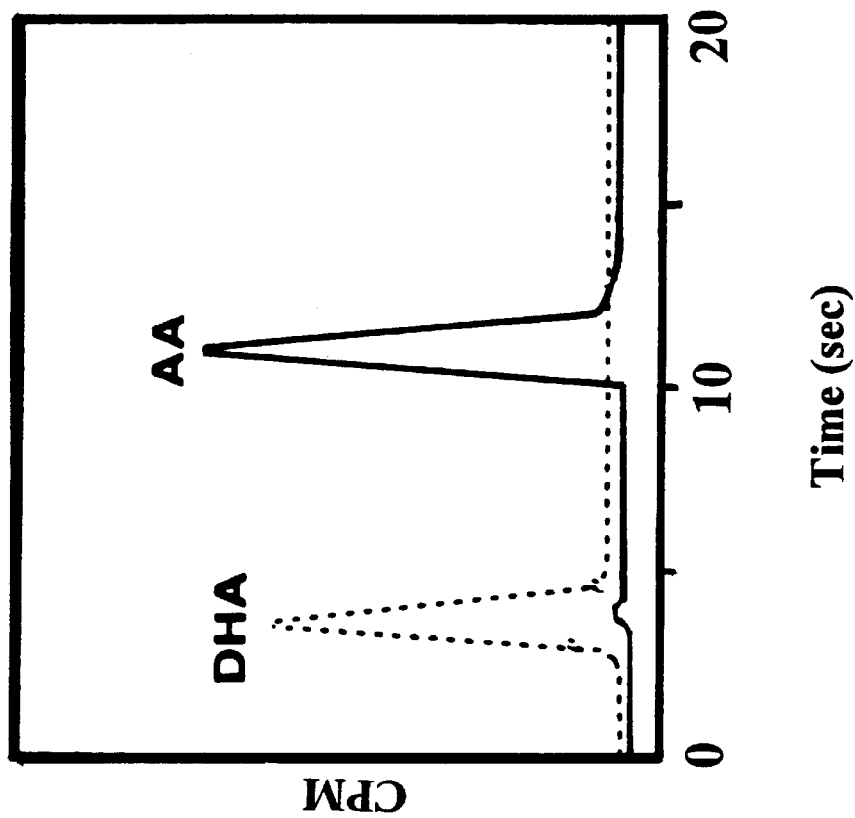
Figure 1F:
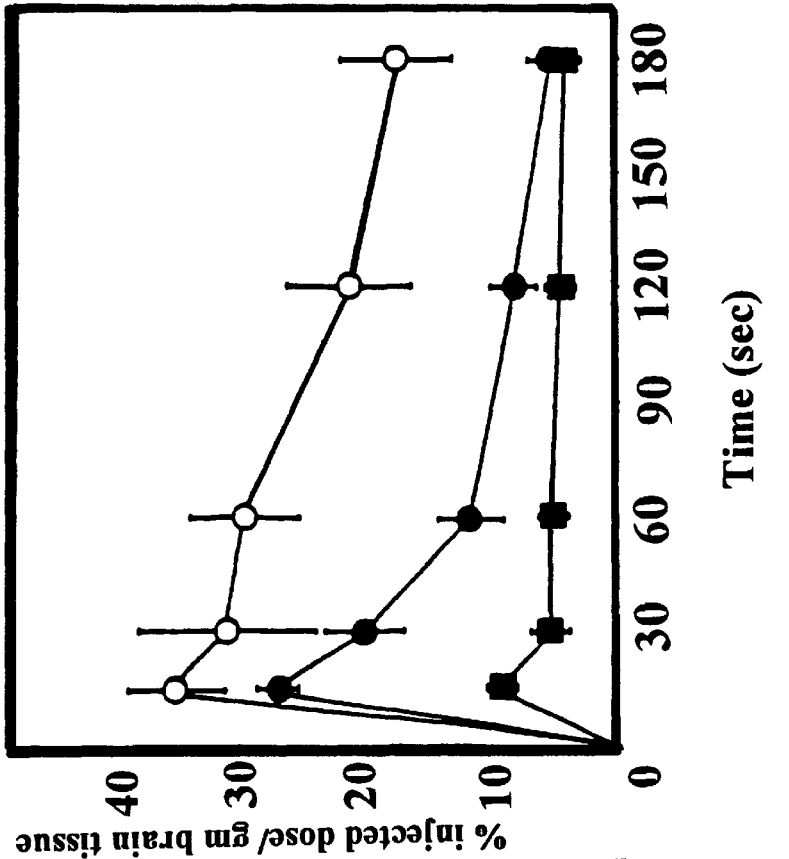
Figure 1E:
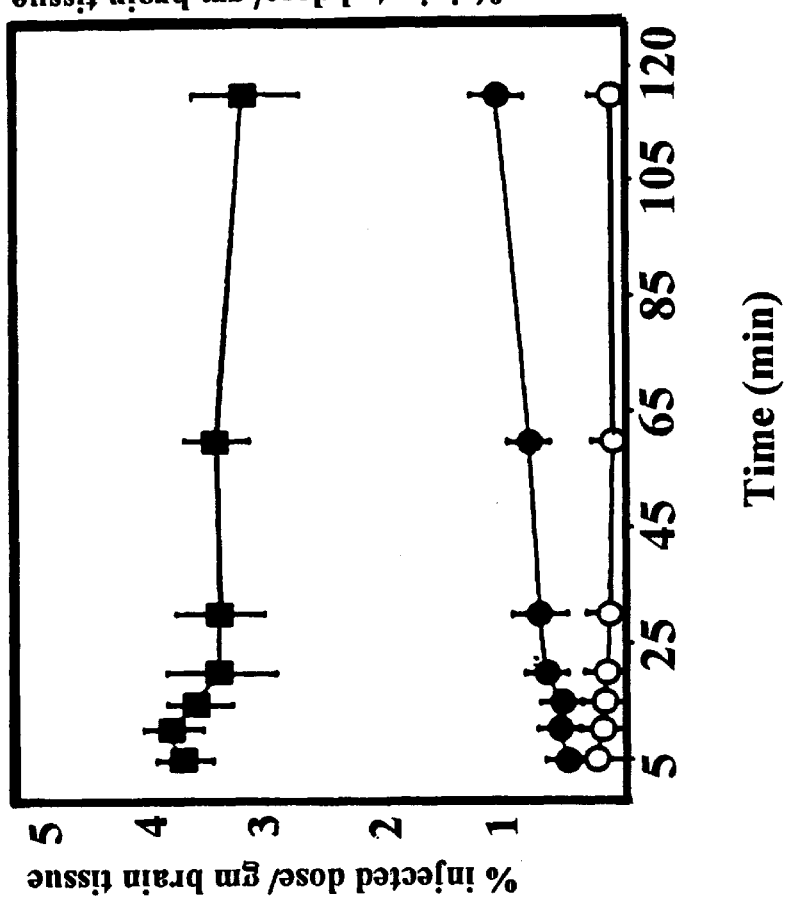
Figure 1H:
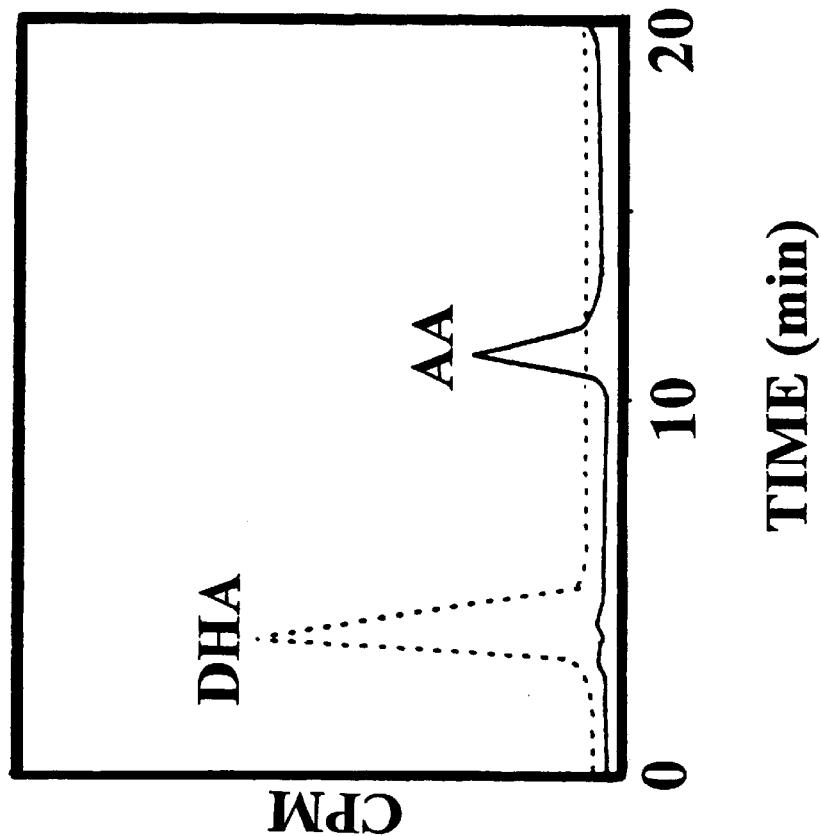
Figure 1G:
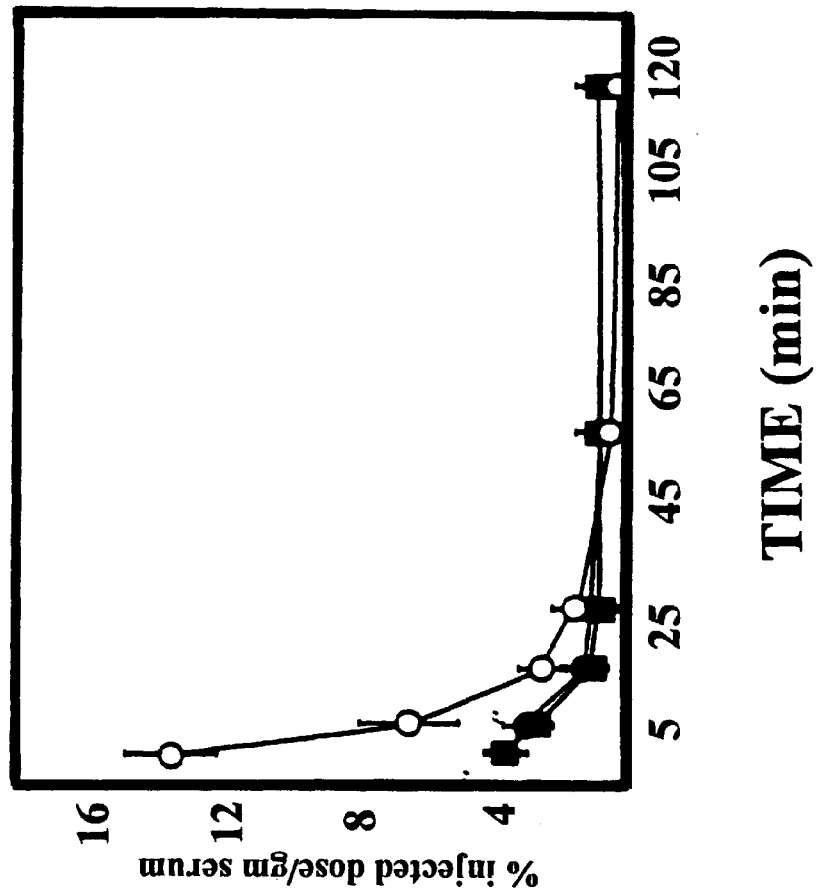

Brain radioactivity, after dehydroascorbic acid injection, reached a maximum of 4.3% of ID/gram brain tissue at 3 min, decreased to 3.3% at 25 min, and remained at that level for up to 2 hours after injection (FIGS. 1D, 1E). Injection of sucrose and ascorbic acid resulted in a maximum brain accumulation of 0.4% ID/gram brain tissue at 15 to 30 seconds after injection (FIG. 1D). Brain radioactivity in the sucrose-injected animals decreased to <0.1% after 15 min, concomitant with the fall in serum radioactivity in these mice (FIGS. 1E, 1G). In ascorbic acid-injected mice there was an increase in brain radioactivity to 1.1% ID/gram brain tissue 2 hours after injection, a time period during which there was a decreasing amount of radioactivity in the serum (FIGS. 1E, 1G). The serum radioactivity concentration at 15 seconds after dehydroascorbic acid injection was 8% ID/gram serum, whereas the corresponding figure in mice injected with ascorbic acid was 27%. Thus dehydroascorbic acid was cleared from the circulation substantially faster than ascorbic acid (FIG. 1F). At the 3-min time point the radioactivity in the serum of the ascorbic acid and dehydroascorbic acid-injected animals was equivalent (FIG. 1G). Radioactivity remaining in the serum of the dehydroascorbic acid-injected animals at 5 min was associated with ascorbic acid (FIG. 1H).

Injected $^{14}$C-ascorbic acid showed no measurable transport into the brain over the first 30-min, but some radioactivity accumulated in the brain at longer time periods. There are at least three potential explanations for this result. The first is that the ascorbic acid was metabolized in the interval time period and the counts in the brain represented transported radiolabeled metabolic breakdown products of ascorbic acid. Such an explanation is unlikely as the HPLC results demonstrated that the majority of the radioactivity in the dehydroascorbic acid-injected brain was eluted in radioactive peaks consistent with intact ascorbic acid. A second possibility is the presence of a small number of $Na^+$-ascorbate cotransporters at the BBB or choroid plexus, which is unlikely since the accumulation of ascorbic acid did not occur linearly with time, as it would in this case, but only occurred after 30 min (13). The interpretation is that oxidation of ascorbic acid in the microenvironment occurred in vivo leading to the production of dehydroascorbic acid which was then transported across the BBB and retained in the brain as ascorbic acid.

The serum concentration of injected dehydroascorbic acid reached only 20 to 25% of the serum concentration of ascorbic acid or sucrose during the initial several minutes after injection. Sucrose has no transport mechanism, therefore its clearance from the serum was slow. Part of the clearance mechanisms for ascorbic acid and dehydroascorbic acid are through transport, the GLUTs in the case of dehydroascorbic acid and potentially a $Na^+$-ascorbate cotransporter in the case of ascorbic acid (4). The rapid clearance of dehydroascorbic acid from the serum likely reflected the large number of glucose transporters available for transport.

Figure 2B:
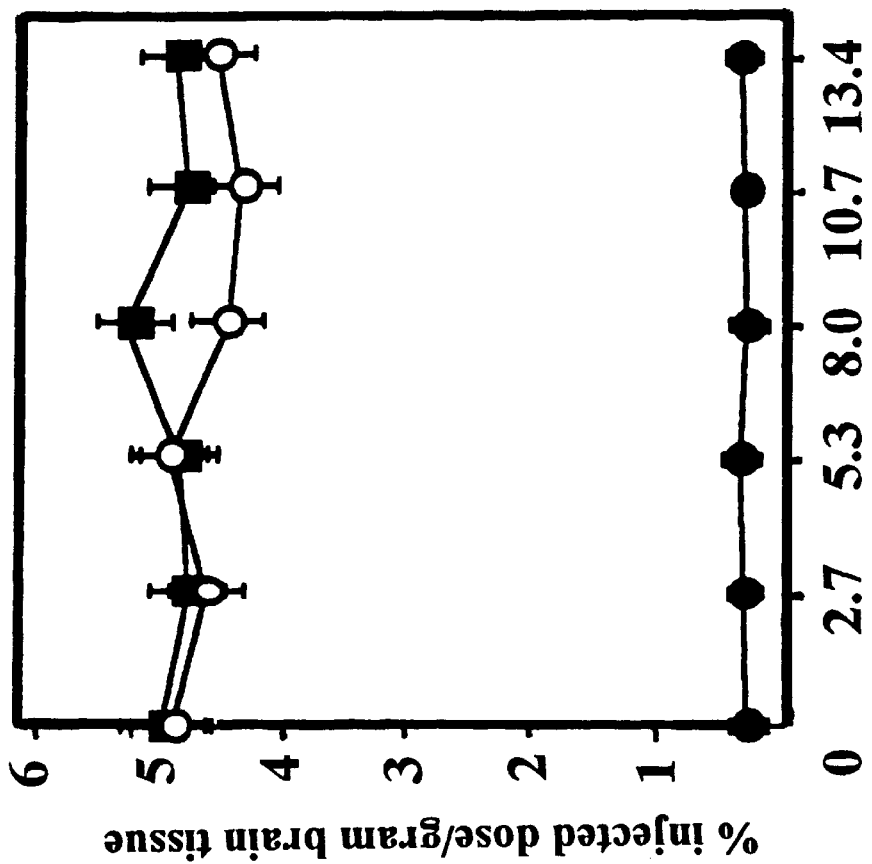
FIG. 2 Specificity of the transport of dehydroascorbic acid through GLUT1 at the Balb/c mouse BBB. (A) $^{14}$C-Dehydroascorbic acid (■) entered the brain and its accumulation was blocked by increasing amounts of D-deoxyglucose which is transported through GLUT1. Transport of $^{3}$H-leucine (○) or $^{14}$C-ascorbic acid (●) across the BBB was not affected by D-deoxyglucose. (B) L-glucose, which is not transported through GLUT1, had no effect on the transport of $^{14}$C-dehydroascorbic acid. Transport of $^{3}$H-leucine (○) or $^{14}$C-ascorbic acid (●) across the BBB was not affected by L-glucose. All experiments were carried out over a 30-second time course. Each data set included 4 mice and the data were expressed as mean±SEM. A mouse has a baseline serum glucose concentration of approximately 12 mM, which calculates to 2.67 mg glucose in the entire mouse based on the average plasma volume of the mouse. The amount of exogenous glucose administered in this experiment was based on this number and subsequent multiples to a maximum tolerable level.
Figure 2A:
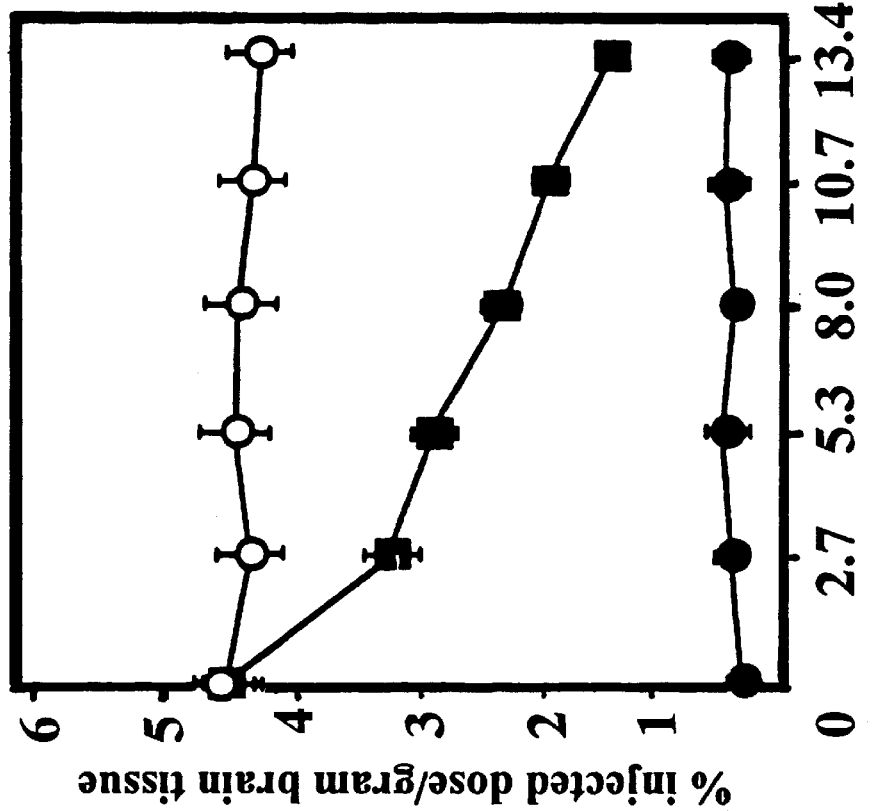
Figure 4:
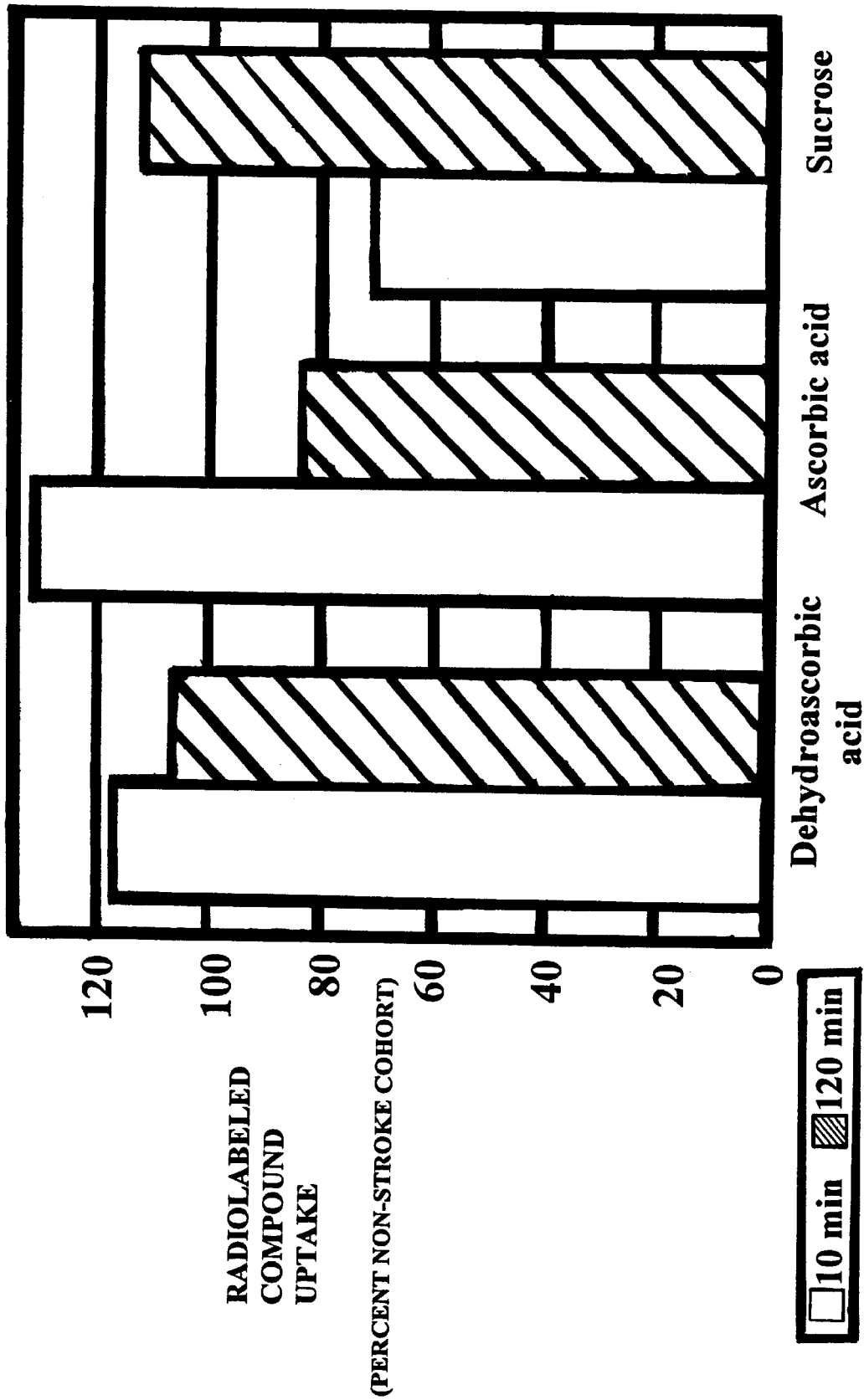
FIG. 4 Tracer studies revealed accumulation of nearly 4% of the DHA (expressed as percent of injected dose (TD) per gram of brain tissue) compared to only trace levels of ascorbic acid and sucrose in ischemic animals.
Figure 5A:
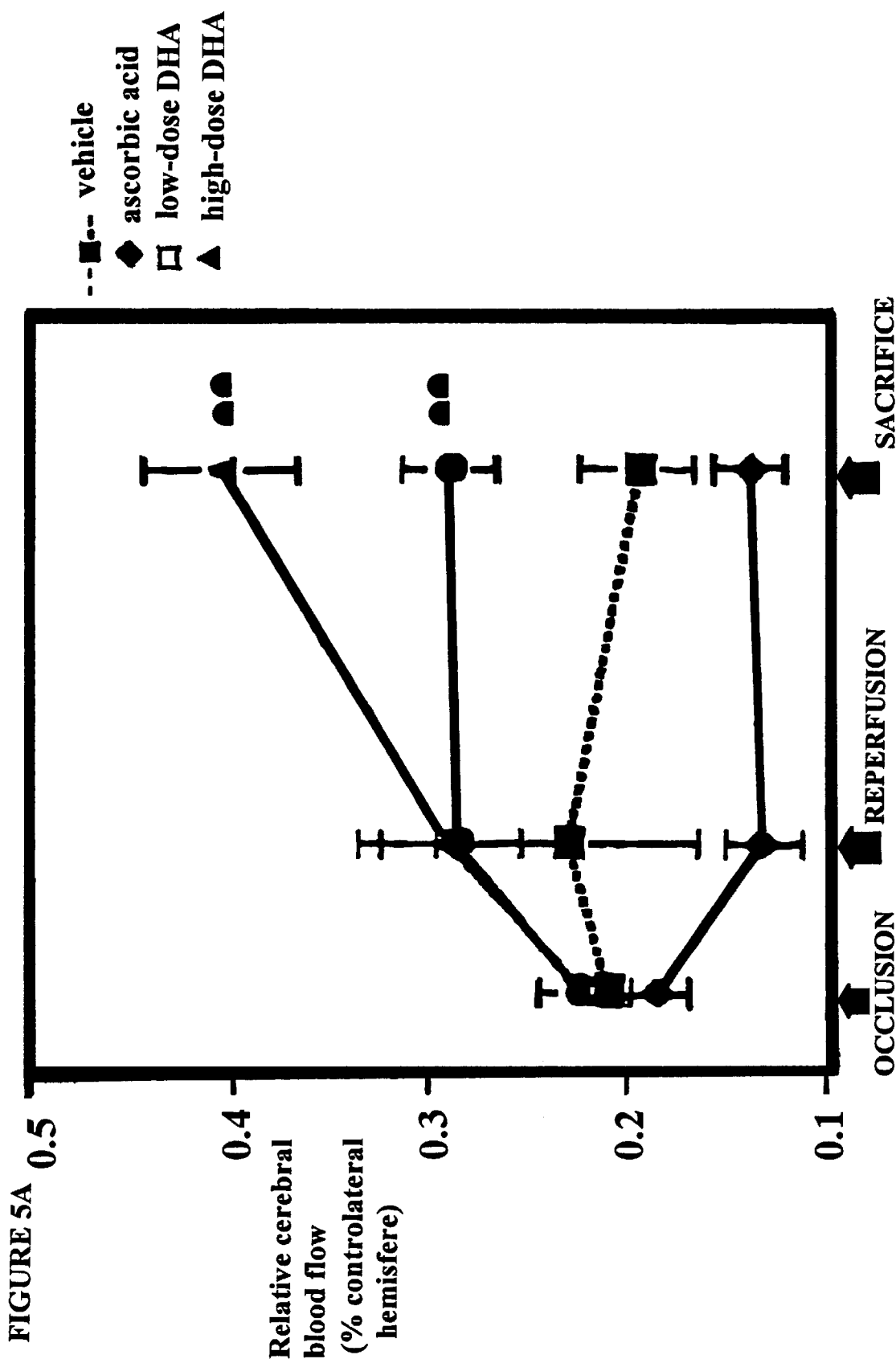
FIG. 5
Figure 5B:
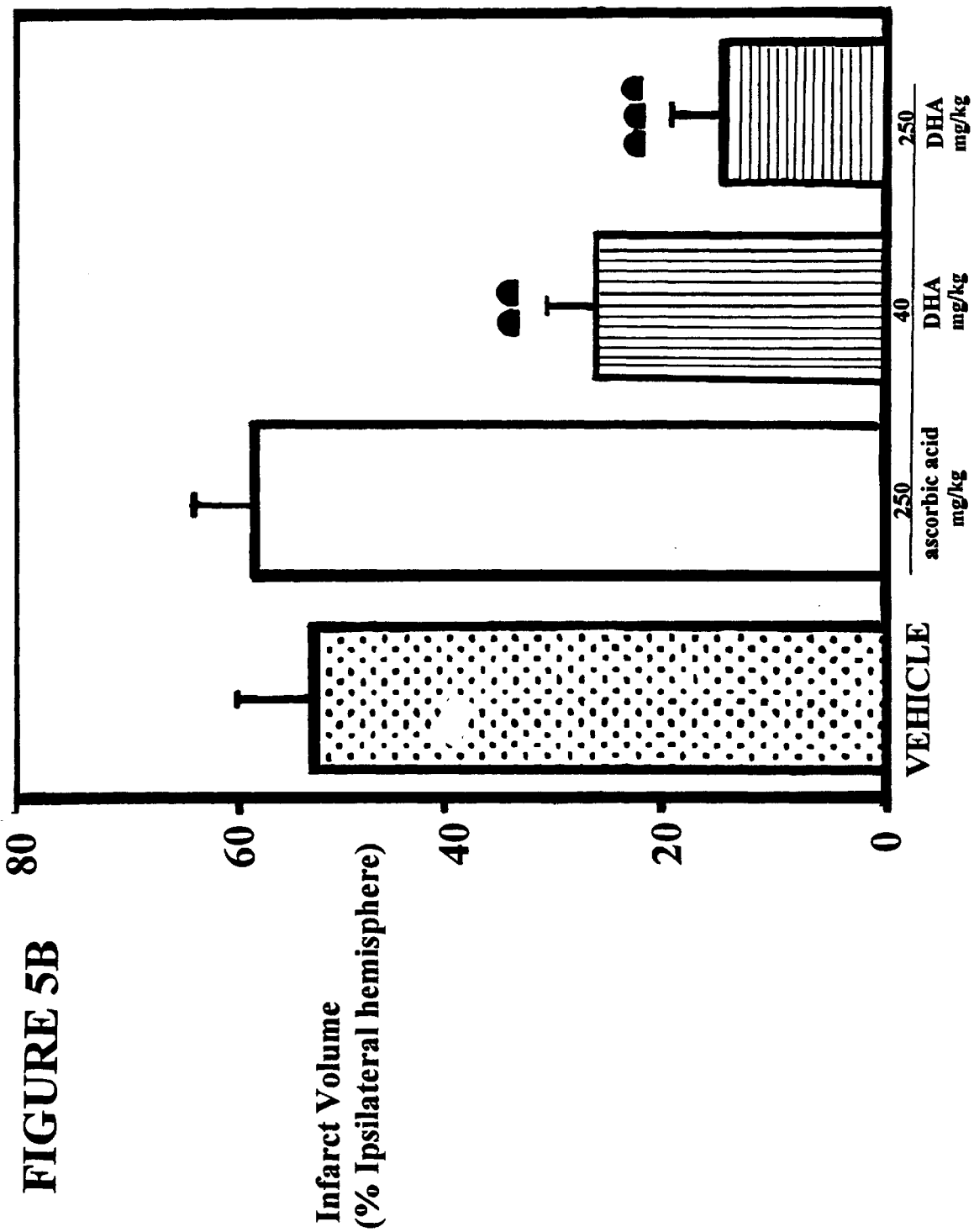
Figure 5C:
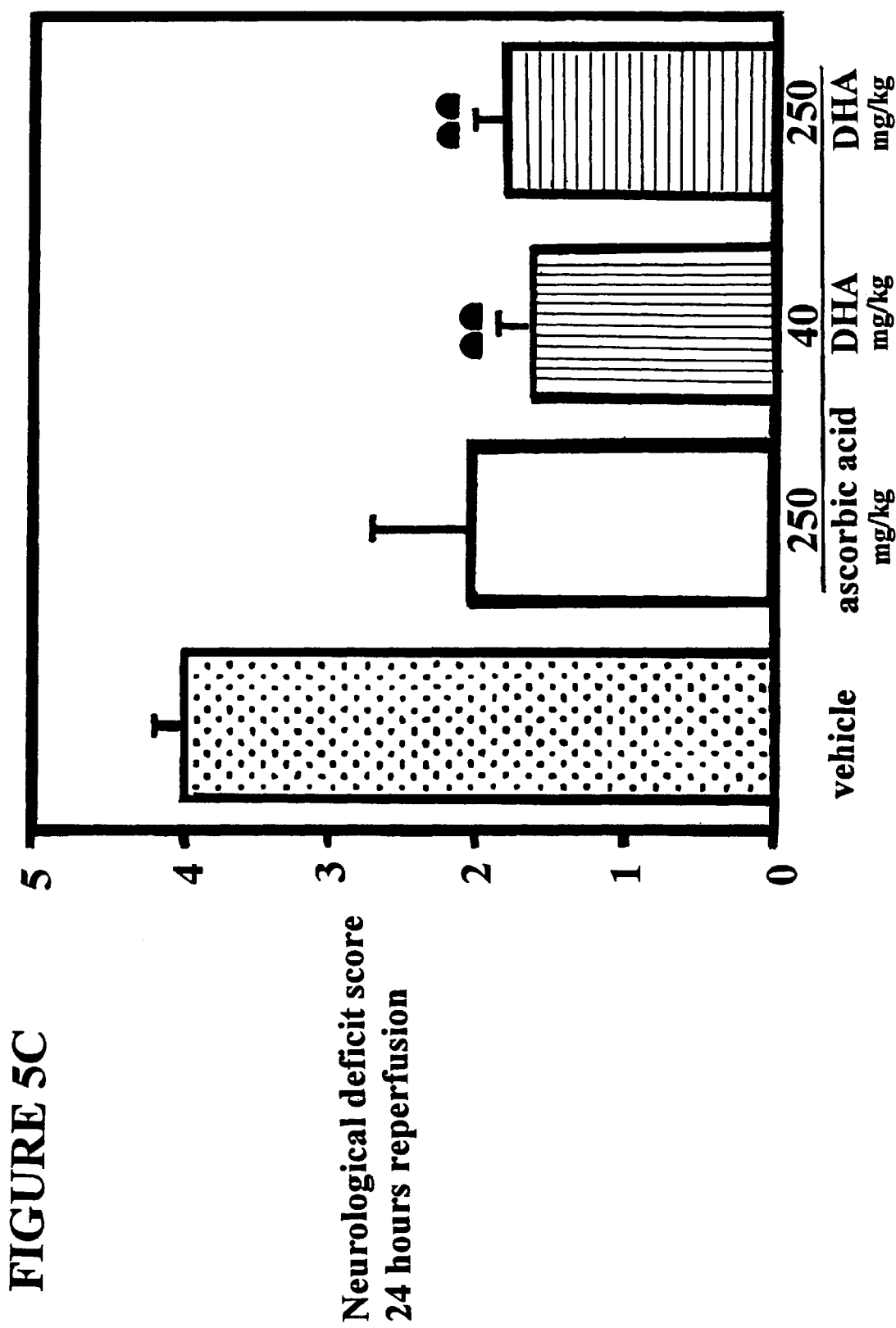
Figure 5D:
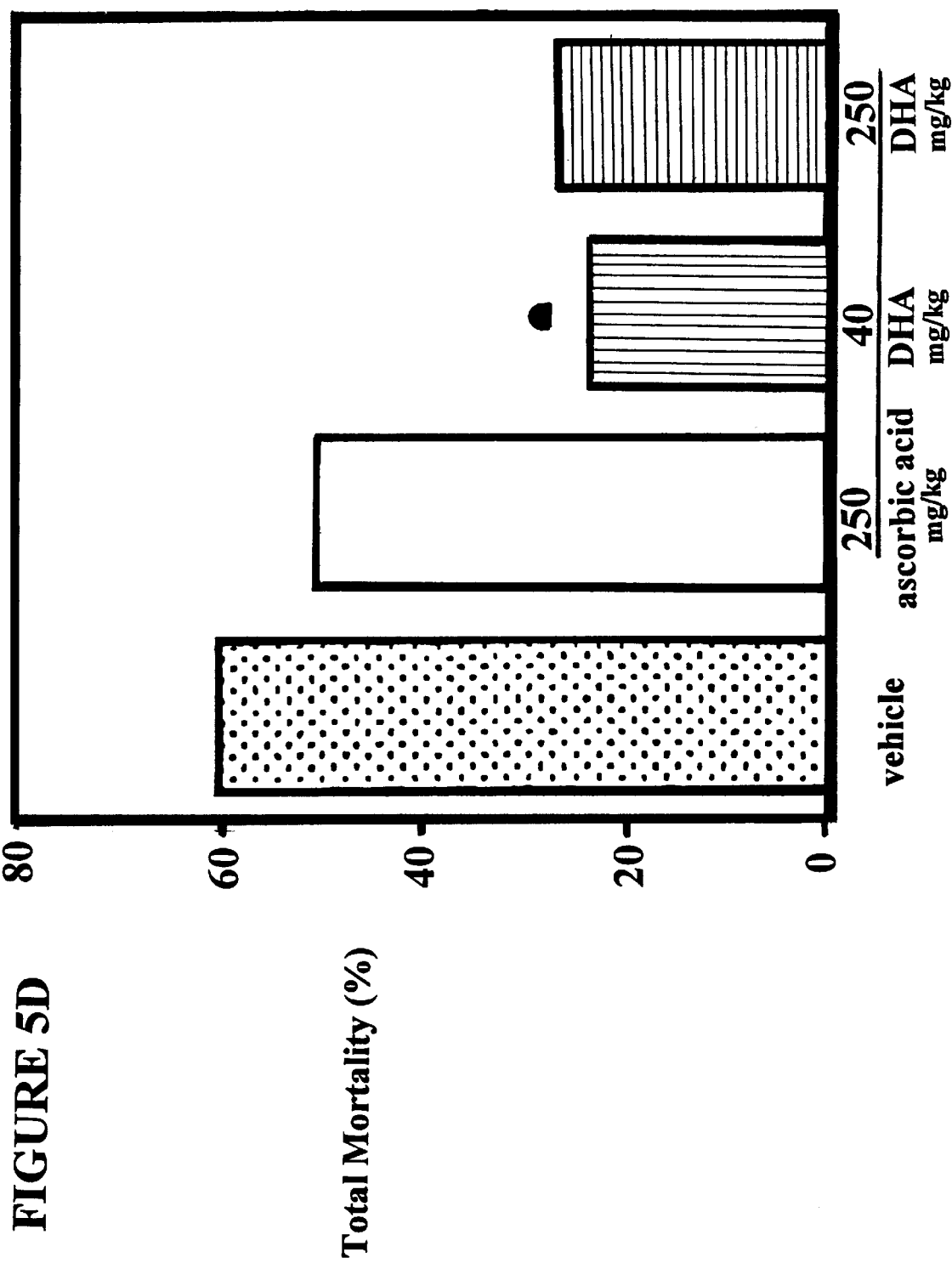

The glucose transporter GLUT1 selectively transports D-glucose but not L-glucose. In order to confirm that dehydroascorbic acid passed the BBB through GLUTs, inhibition experiments were conducted with D- and L-glucose. 2-Deoxy-D-glucose (D-deoxyglucose) and D-glucose (data not shown) inhibited uptake of dehydroascorbic acid in the brain in a dose-dependent fashion up to 70%, whereas L-glucose and leucine had no effect (FIG. 2A). The uptake of leucine, which is not transported by GLUTs, but crosses the BBB largely through L system transporters and to a minor extent by the ASC system transporter (14), was not affected by increasing concentrations of L-glucose of D-deoxyglucose (FIG. 2B) nor were the serum concentrations of ascorbic acid, dehydroascorbic acid and leucine affected by increasing concentrations of D-deoxyglucose or L-glucose (data not shown). These results established that D-deoxyglucose inhibits dehydroascorbic acid from entering the brain through the glucose transporters but does not affect certain other transport systems or alter general BBB permeability by osmotic effects.

The external organ approach, utilizing serum as the external organ, was used to calculate the BBB permeability-surface areas product (PS) in the Fischer F344 rat (15). The calculated PS of $^{14}$C-dehydroascorbic acid was 136±12 (SEM) μl/min/gm brain tissue, $^{14}$C-ascorbic acid was −0.44±0.24 μl/min/gm brain tissue, and $^3$H-D-deoxyglucose was 44±3.2 μl/min/gm brain tissue. The difference in the BBB permeability-surface area products (PS) between ascorbic acid and dehydroascorbic acid illustrated the marked differences in the BBB transport between the redox states of vitamin C. The calculated PS of ascorbic acid was approximately 0 μl/min/gm brain tissue at 30 seconds, similar to sucrose, which indicates no transport across the BBB. The PS of dehydroascorbic acid was 3-fold greater than D-deoxyglucose which corresponds with the difference in the $K_m$ values between the two compounds. The apparent $K_m$ of D-deoxyglucose for transport was 2.5 mM in HL60 cells compared with an apparent $K_m$ of 0.85 mM for dehydroascorbic acid in HL60 cells (2,3).

Digital autoradiography of the brain of a rat injected with $^{14}$C-dehydroascorbic acid and a rat injected with $^{14}$C-ascorbic acid was performed to confirm the anatomical distribution of the injected compounds (FIG. 3).

Autoradiographic evidence of activity accumulation in the brain was seen only in animals injected with dehydroascorbic acid. $^{14}$C-sucrose was used as a marker of intravascular volume.

The results of this study established that the transport of vitamin C into the brain is mediated by GLUTs at the BBB which transport dehydroascorbic acid. Ascorbic acid itself is not transportable across the BBB. The glucose transport in vivo therefore was found to function comparably to in vitro models in that only the oxidized form of vitamin C, dehydroascorbic acid, was transportable (1–3). Dehydroascorbic acid was reduced to ascorbic acid after passing the BBB and was retained in the brain as ascorbic acid. This trapping mechanism allows for the accumulation of higher concentrations of vitamin C in the brain than in the blood. Overall, the findings point to the oxidation of ascorbic acid as being the critical step in the regulation of the accumulation of vitamin C in the brain.

The current recommended daily allowance of vitamin C is 60 mg daily and yields a steady-state plasma concentration of approximately 24 μM in human volunteers (16). Only ascorbic acid is detected in the serum, with dehydroascorbic acid at trace serum levels or not measurable (17). The vitamin C injected in this study was approximately 500 μM, which is 5-fold greater than the physiologic serum concentration of vitamin C in rodents (18). In this study, at physiologic glucose concentrations, dehydroascorbic acid transport through GLUT1 did occur. The serum concentration of glucose in normal rodents is approximately 10 mM yet there is still dehydroascorbic acid transport to the brain indicating that both dehydroascorbic acid and glucose are substrates of the GLUTs under physiologic conditions. This result is consistent with in vitro data demonstrating that a deoxyglucose concentration greater than 50 mM is necessary to block the transport of dehydroascorbic acid through GLUT1 (2,3).

James Lind detailed the clinical description of scurvy in A Treatise of the Scurvy in 1772. He concluded his report of the autopsy results of scorbutic patients' "ravaged bodies" as follows, "What was very surprising, the brains of those poor creatures were always sound and entire . . . " (19). There thus appeared to be a mechanism for the accumulation and storage of ascorbic acid in the brain such that the brain would be the last organ depleted of vitamin C. The normal human brain has a vitamin C concentration of approximately 1 mM, 10 times the normal serum concentration (20). The precise role of vitamin C in the brain is uncertain, but ascorbic acid may be a cofactor of dopamine β-hydroxylase and is thus involved in the biosynthesis of catecholamines. Vitamin C can also inhibit the peroxidation of membrane phospholipids and act as a scavenger of free radicals in the brain (21,22). The results of this study demonstrate the physiological importance of vitamin C transport through GLUT1 in the form of dehydroascorbic acid and define the mechanism by which the brain obtains and retains vitamin C.

Recent data show that large quantities of vitamin C can be loaded into the brain. An experiment was done in which the carotid artery of a subject rat was cannulated with a catheter and 24 mg of dehydroascorbic acid was injected into the artery. The injected dehydroascorbic acid was spiked with a tracer amount of radioactive ($^{14}$C-labeled) dehydroascorbic acid. The dehydroascorbic acid was infused over forty minutes and the brain was harvested. The amount of radioactive vitamin C was quantitated in the brain and total amount of injected vitamin C that accumulated in the brain was thus extrapolated. The experiment demonstrated that 2.6 mg of vitamin C accumulated in the brain of the subject rat during the forty minute injection period, which was approximately 11% of the injected dose. This shows that it is possible to achieve pharmacologic concentrations of vitamin C in the brains of subject animals. It is of note that the total vitamin C concentration in the normal adult rat brain is approximately 150 µg. A log-fold greater Vitamin C than baseline normal concentration of Vitamin C was thus achieved.

REFERENCES AND NOTES

1. Vera, J. C., C. I., Fischbarg J. & Golde, D. W. *Nature* 364, 79–82 (1993).
2. Vera, J. C., Rivas, C. I., Zhang, R. H., Farber, C. M. & Golde, D. W. *Blood* 84, 1628–1634 (1994).
3. Vera, J. C. et al. *J. Biol. Chem.* 270, 23706–23712 (1995).
4. Diliberto, E. J., Jr., Heckman, G. D. & Daniels, A. J. *J. Biol. Chem.* 258, 12886–12894 (1983).
5. Crone, C. *J. Physiol.* 181, 103–113 (1965).
6. Pardridge, W. M., Boado, R. J. & Farrell, C. R. *J. Biol. Chem.* 265, 18035–18040 (1990).
7. Ehrlich, P. *Das Sauerstoff-Bedurfnis des Organismus: eine Farbenanalytische Studie* (Hirschwald, Berlin, 1885).
8. Ehrlich, P. in Collected Studies in *Immunity* 567–595 (John Wiley, New York, 1902).
9. Brightman, M. W. *Exp. Eye Res.* 25 Suppl., 1–25 (1977).
10. Reese, T. S. & Karnovsky, M. J. *J. Cell Biol.* 34, 207–217 (1967).
11. Pardridge, W. M. *Physiol. Rev.* 63, 1481–1535 (1983).
12. Triguero, D., Buciak, J. B. & Pardridge, W. M. *J. Neurochem.* 54, 1882–1888 (1990).
13. Spector, R. & Lorenzo, A. V. *Am. J. Physiol.* 225, 757–763 (1973).
14. Cangiano, C. et al. *J. Biol. Chem.* 258, 8948–8954 (1983).
15. Van Uitert, R. L., Sage, J. I., Levy D. E. & Duffy T. E. *Brain Res.* 222, 365–372 (1981).
16. Levine, M. et al. *Proc. Natl. Acad. Sci. U.S.A.* 93, 3704–3709 (1996).
17. Dhariwal, K. R., Hartzell, W. O. & Levine, M. *Am. J. Clin. Nutr.* 54, 712–716 (1991).
18. Stubbs, D. W. & McKernan, J. B. *Proc. Soc. Exp. Biol. Med.* 125, 1326–1328 (1967).
19. Stewart, C. P. & Guthrie, D. *Lind's Treatise on Scurvy* (Edinburgh University Press, Edinburgh, ed. 1, 1953).
20. Hornig, D. Ann. *N. Y. Acad. Sci.* 258, 103–118 (1975).
21. Kaufman, S. *Pharmacol, Rev.* 18, 61–69 (1966).
22. Schreiber, M. & Trojan, S. *Physiol. Res.* 40, 413–418 (1991).
23. Kawamoto, T. & Shimizu, M. *Stain Technology* 61, 169–183 (1986).
24. Abdel el Motal, S. M. & Sharp, G. W. *Endocrinology* 116, 2337–2340 (1985).
25. Hsu, W. H. & Hummel, S. K. *Endocrinology* 109, 825–829 (1981).
26. Jenner, P. *Lancet* 344, 796–798 (1994).
27. Sano, M. et al. *The New England Journal of Medicine* 336, 1216–1222 (1997).
28. Thomas, T., Thomas, G., McClendon, C., Sutton, T., and Mullan, M., *Nature* 380, 168–171 (1996).
29. Lethem, R. and Orrell, M. *Lancet* 349, 1189–1190 (1997).
30. Department of Neurology, University of Rochester Medical Center, *New Engl. J. Med.* 328, 176–183 (1993).
31. Youdim, M. B. H., and Riederer, P. *Scientific American* January, 52–59 (1997).
32. Challem, J. *The Nutrition Reporter* (1996).
33. Witzum, J. L. *Lancet* 344, 793–795 (1994).
34. Witztum, J. L. *Br. Heart J., Jan*:69 (1 Suppl):S12–18 (1993).
35. Peyser C. E., Folstein, M., Chase, G. A., Starkstein, S., Brandt, J., Cockrell J. R., Bylsma, F., Coyle, J. T., McHugh, P. R., Folstin, S. E. *Am J. Psychiatry*, 152 1771–1775.
36. Tardif, J.-C. et al., *New Engl. J. Med.* 337, 365–372 (1997).
37. McCord, J. M. *New Engl. J. Med.* 312, 159–163 (1985).

Second Series of Experiments

Although stroke is the leading cause of permanent morbidty worldwide(1), current therapy is limited to thrombolysis, with a narrow therapuetic window and requirement for sophisticated pretreatment imaging. (2,3) Acute restoration of flow can also lead to the production of reactive oxygen species, which are directly toxic to neurons and glia, and may exacerbate leukocyte accumulation, (4) microvascular thrombosis, and nitric-oxide mediated injury. (5–7) Efforts to abrogate oxidant stress are complicated by the limited ability of antioxidants to cross the blood brain-barrier. (9) Previous work has defined the dehydroascorbic acid (DHA)-GLUT1 transport mechanism by which cells accumulate and retain vitamin C, (9, 17) a potent anitoxidant known to quench free radicals in the setting of ischemia. (10) More recently, the rapid transport of DHA across the blood-brain barrier and its retention in the brain as ascorbic acid was described in rodents. (11) Here, we describe the ability of DHA, given intravenously in the setting of murine stroke to improve cerebral blood flow, functional outcome, and the volume of infarcted brain tissue. The level of protection achieved is far greater than that seen with ascorbic acid administration, supporting our hypothesis that the use of a potent antioxidant, with clearly defined blood brain-barrier penetrability, may have a role in the treatment of thromboembblic stroke in humans.

Radiolabeled dehydroascorbic acid (DHA) was generated by incubating $^{14}$C-ascorbic acid with ascorbate oxidase, 1 unit/1.0 mmol L-ascorbate (derived from Cucurbita species, Sigma). Dithiothreitol (0.1 mmol/L) was then added separately to both DHA and ascorbate prior to use as a reducing agent. For experiments examining the effect of focal cerebral ischemia on the DHA's ability to: (1) cross the blood-brain barrier and, (2) protect cerebral tissue, we employed an intraluminal murine model of reversible (45 minutes) or permanent (24 h) right middle cerebral artery occlusion. (12) Anesthetized normothermic C57/6J BL mice were treated prior to ischemia via penile injection with either high dose DHA (250 mg/kg), low dose DHA (40 mg/kg), ascorbate (250 mg/kg), or sucrose (a non-metabolized, non-transportable marker of plasma volume). All animals underwent transcranial laser doppler measurement of cortical cerebral blood flow perioperatively. Nine mice were subjected to 10 minutes or two hours of focal ischemia and immediately sacrificed in order to assess DHA (n=3), ascorbate (n=3), and sucrose (n=3) transport as measured by radiation scintillation counting using 5 $\mu$Ci of $^{14}$C-ascorbic and (L-[1-$^{14}$C]-ascorbic acid, specific activity, 6.6 mCi/mmol, Dupont NEN), $^{14}$C-DHA or $^{3}$H-sucrose ([fructose-1-$^{3}$H]-sucrose, specific activity 20.0 Ci/mmol., Dupont NEN) as previously described. (11) In contrast, the experimental cohorts were followed for 24 hours and underwent pre-sacrifice neurological examination, as previously described. $^{13}$Infarct volumes were calculated by digital analysis of serial, 2,3,5-triphenyltetrazolium-stained, sections, with volumes expressed as percentage of the ipsilateral hemisphere.$^{12}$ There were 67 animals in the reperfusion cohort (including vehicle, 40 mg/kg DHA, 250 mg/kg DHA, and 250 mg/kg ascorbate cohorts) and 54 animals in the non-reperfused cohort (including vehicle, 250 mg/kg DHA, and 250 mg/kg ascorbate cohorts). Comparisons were made between groups with a two-tailed Student t-test for unpaired variable. All studies were performed in accordance with an institutionally approved animal protocol.

Tracer studies revealed accumulation of nearly 4% of the DHA (expressed as percent of injected dose (TD) per gram of brain tissue) compared to only trace levels of ascorbic acid and sucrose in ischemic animals, a finding not significantly different from that seen in sham-operated animals (FIG. 1). Previous studies demonstrated that the form of vitamin C accumulating in the brains of DHA-injected animals is >85% ascorbic acid as a result of reduction of transported DHA. (11) Both high (250 mg/kg) and low dose (40 mg/kg) DHA pre-treatment of animals undergoing reperfused stroke, demonstrated a dose-dependent improvement in post-ischemic cerebral perfusion compared to both sucrose and ascorbic acid treated animals (19±3% vehicle, 13±1% AA, 28±2% low-DHA, 40±4% high-DHA; p<0.05 for either DHA vs. either control) (FIG. 2A). In addition, DHA conferred dose-dependent cerebroprotection as evidenced by both decreased cerebral infarct volumes (54±6% vehicle, 58±4% AA, 22±4% low-DHA, 12±4% high-DHA; p<0.05 for either DHA vs. either control) (FIG. 2B) and reductions in neurological deficit scores (4.0±0.2 vehicle, 2.7±0.7 AA, 1.6±0.2 low-DHA, 1.9±0.2 high-DHA; p<0.05 for either DHA vs. vehicle) (FIG. 2C). In contrast, ascorbic acid treatment was not associated with significant improvements in either infarct size or neurological function, nor did ascorbic acid treatment reduce overall mortality as was the case with DHA (FIG. 2D). Ascorbic acid treated animals died at nearly twice the rate of the DHA-treated cohort (60% vehicle, 50% AA, 24% low-DHA, 27% high-DHA; p<0.05 for low-DHA vs. vehicle).

Since clinical therapeutic antioxidant strategies might be employed prior to hospitalization and reperfusion, we examined the effect of high-dose DHA on non-reperfused stroke as well. As in the prior set of experiments, high-dose DHA improved pre-sacrifice regional cerebral cortical perfusion whereas ascorbic acid did not (13±2% vehicle 15±3% AA, and 30±3% high-DHA; p<0.05 for DHA vs. either control). This improved perfusion was associated with similar reductions in infarct volume (51±6% vehicle, 46±6% AA, and 26±5% high-DHA, p<0.01 vs. vehicle), and sacrifice neurological deficit scores (3.0±0.3% vehicle, 3.2±0.4% AA, and 1.9±0.2% high-DHA; p<0.005 for DHA vs. either control). As in the setting of reperfusion, DHA reduced mortality by nearly 50% (50% vehicle, 64% AA, and 30% high-DHA.

Therapeutic, non-enzymatic scavenging of free radicals can be accomplished by ascorbic acid but only at supraphysiologic concentrations. (10) We confirmed previous findings that intravenous administration of DHA allows supraphysiologic concentrations of ascorbate to be achieved in the brain whereas ascorbic acid administration does not. (11) Importantly, our results demonstrate the in vivo cerebroprotection conferred by DHA in the setting of both transient and permanent, focal cerebral ischemia. In doing so these data further implicate the role of ascorbate in free radical scavenging following cerebral ischemia, (14, 15) and underscore the importance of pharmacologically increasing cerebral vitamin C concentrations following cerebral ischemia. (14,16) These data also support the notion that local ascorbate may be critical in limiting nitric-oxide signaling failure mediated by superoxide, since DHA had a dose-dependent effect on cerebral blood flow. (10) Maintenance of microvascular potency by stabilizing NO-dependent vascular signalling requires very high local levels of ascorbate, since the reaction of ascorbate with superoxide is $10^5$-fold slower than that of superoxide with SOD and certainly NO. Together with previous work this study also suggests that the 10–100 mmol/L concentrations of acrorbate predicted to inhibit superoxide-dependent vasoconstriction can be achieved with the administration of DHA but not ascorbic acid. (10,11) DHA's ability to improve perfusion in ischemic beds subjected to both transient and permanent ischemia has major implications for the treatment of progressive microvascular failure in the setting of clinical stroke.

References for Second Series of Experiments

1. Bronner, L., Kanter, D. & Manson, J. *N Engl J Med* 333, 1392–1400 (1995).
2. The National Institute of Neurological Disorders and Stroke rt-PA Stroke Study Group, *N Engl J Med* 333, 1581–1587 (1995).
3. Chiu, D., Krieger, D., Villar Cordova, C., et al. *Stroke* 29, 18–22 (1998).
4. Prestigiacomo, C. J., Kim, S. C., Connolly, E. S. J. & Pinsky, D. J. *Stroke* 30, 1110–1117 (1999).
5. Matsuo, Y., Kihara, T., Ikeda, M., Ninomiya, M., Onodera, H., & Kogura, K. *Journal of Cerebral Blood Flow and Metaoblism* 15, 941–947 (1995).
6. Choudhri, T. F., Hoh, B. L., Zerwes. H. G., et al. *J. Clin Invest* 102, 1301–1310 (1998).
7. Wolin, M. S., Davidson, C. A., Kaminski, P. M., Fayngersh, R. P. & Mohazzab-H, K. M., *Biochemistry (Moscow)* 63(7), 958–965 (1998).
8. Hall, Ed, Andrus, P K, Smith, S L, et al. *Acta Neurochirugica-Supplementum* 66, 107–113 (1996).
9. Vera J C, Rivas C I, Fischbarg J, Golde D W, *Nature* 364(6432), 79–82 (1993).
10. Jackson, T. S., Xu, A., Vita, J. A. & Keaney, J. F. Jr. *Circ. Res.* 83, 916–922 (1998).
11. Agus, D. B., Gambhir, S. S., Pardridge, W. M., et al. *J. Clin. Invest.* 100(11), 2842–2848 (1997).
12. Connolly, E. S. J., Winfree, C. J., Stern, D. M., Solomon, R. A. & Pinsky, D. J. *Neurosurgery* 38(3), 523–532 (1996).
13. Huang, Z., Huang, P. L., Panahian, N., Dalkara, T., Fishman, M. C. & Moskowitz M. A. *Science* 265, 1883–1885 (1994).
14. Oriot, D., Beharry, K., Gordon, J. B. & Aranda, J. V. *acta Paediatrica* 84, 621–626 (1995).
15. Flamm, E. S., Demopoulos, H. B., Seligman, M. L., Poser, G. R. & Ransohoff, J. *Stroke* 9, 445–447 (1978);
16. Pietronigro, D D, Demopoulos, H B Hovsepian, M & Flamm, E S *Stroke* 13, 8 (1982) (Abstract).

17. Vera, J. C. C. J. Rivas, F. V. Velasquez, R. H. Zhang, I. J. Concha, and D. W. Golde 1995, Resolution of the facilitated transport of dehydroascorbic acid from its intracellular accumulation as ascorbic acid. *J. Biol chem* 270:23706–23712

What is claimed:

1. A method of treating or preventing a disease involving free radicals in a subject which comprises administering to the subject an amount of dehydroascrobic acid or a salt thereof effective to increase the concentration of ascorbic acid in a cell, wherein the disease is selected from the group consisting of cancer, cardiovascular disease and a cataracts condition, so as to thereby treat or prevent the disease involving free radicals in the subject.

2. A method of treating or preventing a disease involving free radicals in a subject which comprises administering to the subject an amount of dehydroascrobic acid or a salt thereof effective to increase the antioxidant potential of a cell, wherein the disease is selected from the group consisting of cancer, cardiovascular disease and a cataracts condition, so as to thereby treat or prevent the disease involving free radicals in the subject.

3. The method of claim 1 or 2, wherein the cancer is selected from the group consisting of prostate cancer, biliary tract cancer, brain cancer, glioblastomas, medelloblastomes, breast cancer, cervical cancer, choriocarcinoma, colon cancer, endometrial cancer, esophageal cancer, gastric cancer, hematological neoplasms, acute lymphocytic and myelogenous leukemia, multiple myeloma, AIDS associated leukemias, adult T-cell leukemia lymphoma, intraepithelial neoplasms, Bowens' disease, Paget's disease, liver cancer, lung cancer, lymphomas, Hodgkin's disease, lymphozytic lymphomas, neuroblastomas, oral cancer, squamous cell carcinoma, ovarian cancer, pancreas cancer, rectal cancer, sarcomas, leiomyosarcoma, rhabdomyosarcoma, liposarcoma, fibrosarcoma, osteosarcoma, skin cancer, melanoma, Kaposi's sarcoma, basocellular cancer, squamous cell cancer; testicular cancer, stromal tumors, germ cell tumors, thyroid cancer, thyroid adenocarcinoma, medullar carcinoma, renal cancer, adenocarcinoma and Wilms tumor.

4. The method of claim 1 or 2, wherein the cardiovascular disease is selected from the group consisting of atherosclerosis, post-myocardial infarction, post-angioplasty, and thrombolytic reperfusion.

5. The method of claim 1 or 2, wherein the cataracts condition is corneal opacification.

6. A method of slowing the aging process of a subject which comprises administering to the subject an amount of dehydroascrobic acid or a salt thereof effective to increase the concentration of ascrobic acid in a cell, so as to thereby slow the aging process of the subject.

7. A method of slowing the aging process of a subject which comprises administering to the subject an amount of dehydroascrobic acid or a salt thereof effective to increase the antioxidant potential of a cell, so as to thereby slow the aging process of the subject.

8. A method of treating or preventing human immunodeficiency virus in a subject which comprises administering to the subject an amount of dehydroascrobic acid or a salt thereof effective to increase the concentration of ascorbic acid in a cell, so as to thereby treat or prevent human immunodeficiency virus in the subject.

9. A method of treating or preventing human immunodeficiency virus in a subject which comprises administering to the subject an amount of dehydroascrobic acid or a salt thereof effective to increase the antioxidant potential of a cell, so as to thereby treat or prevent human immunodeficiency virus in the subject.

10. The method of any one of claims 1–2 and 6–9, wherein the subject is a human being.

11. The method of any one of claims 1–2 and 6–9, wherein the dehydroascorbic acid or salt thereof is administered orally, intravenously, subcutaneously, intramuscularly or topically or by liposome-mediated delivery.

12. The method of any one of claims 1–2 and 6–9, which further comprises administering an effective amount of a therapeutic agent.

* * * * *